United States Patent
Saarinen et al.

(10) Patent No.: US 9,320,291 B2
(45) Date of Patent: Apr. 26, 2016

(54) PRODUCTION OF A SACCHARIDE COMPOSITION COMPRISING GLUCANS AND MANNANS BY ALKALINE AND ACID HYDROLYSIS OF YEAST CELLS

(75) Inventors: Juhani Saarinen, Helsinki (FI); Ritva Niemela, Helsinki (FI); Jari Helin, Rajamaki (FI); Jari Natunen, Vantaa (FI); Jukka Hiltunen, Helsinki (FI)

(73) Assignee: GLYKOS FINLAND OY, Helsinki (FI)

( * ) Notice: Subject to any disclaimer, the term of this patent is extended or adjusted under 35 U.S.C. 154(b) by 189 days.

(21) Appl. No.: 13/140,765

(22) PCT Filed: Dec. 18, 2009

(86) PCT No.: PCT/FI2009/051017
§ 371 (c)(1),
(2), (4) Date: Jun. 17, 2011

(87) PCT Pub. No.: WO2010/070207
PCT Pub. Date: Jun. 24, 2010

(65) Prior Publication Data
US 2011/0250235 A1    Oct. 13, 2011

(30) Foreign Application Priority Data
Dec. 18, 2008 (FI) .................................. 20080665

(51) Int. Cl.
| | | |
|---|---|---|
| A61K 45/00 | (2006.01) | |
| A61K 47/00 | (2006.01) | |
| A61K 31/715 | (2006.01) | |
| A61K 36/06 | (2006.01) | |
| A61K 36/064 | (2006.01) | |
| A23L 1/09 | (2006.01) | |
| A23K 1/16 | (2006.01) | |
| A23L 1/30 | (2006.01) | |
| A23L 2/52 | (2006.01) | |
| C08B 37/00 | (2006.01) | |
| C12P 19/04 | (2006.01) | |

(52) U.S. Cl.
CPC ................. *A23L 1/09* (2013.01); *A23K 1/1643* (2013.01); *A23L 1/30* (2013.01); *A23L 1/3016* (2013.01); *A23L 2/52* (2013.01); *C08B 37/0003* (2013.01); *C08B 37/0087* (2013.01); *C12P 19/04* (2013.01)

(58) Field of Classification Search
None
See application file for complete search history.

(56) References Cited

U.S. PATENT DOCUMENTS

| | | | |
|---|---|---|---|
| 4,138,479 A | 2/1979 | Truscheit et al. | |
| 4,343,784 A | 8/1982 | Massot et al. | |
| 4,810,646 A | 3/1989 | Jamas et al. | |
| 5,028,703 A | 7/1991 | Jamas et al. | |
| 5,250,436 A | 10/1993 | Jamas et al. | |
| 5,861,048 A * | 1/1999 | Kamasaka et al. ................. 71/11 |
| 2004/0082539 A1* | 4/2004 | Kelly ............................... 514/54 |
| 2004/0082549 A1* | 4/2004 | Jomaa .............................. 514/114 |
| 2005/0020490 A1* | 1/2005 | Courie et al. ...................... 514/8 |
| 2006/0009501 A1* | 1/2006 | Nair et al. ........................ 514/367 |
| 2006/0263415 A1* | 11/2006 | Sedmak ........................... 424/442 |
| 2011/0045545 A1* | 2/2011 | Yu et al. .......................... 435/101 |

FOREIGN PATENT DOCUMENTS

| | | |
|---|---|---|
| EP | 0515216 A2 | 11/1992 |
| EP | 0950356 A1 | 10/1999 |
| EP | 0950716 B1 | 12/2005 |
| JP | 3002202 A | 1/1991 |
| JP | 5295003 A | 11/1993 |
| JP | 6340701 A | 12/1994 |
| JP | 7051081 A | 2/1995 |
| JP | 2006169514 A | 6/2006 |
| WO | 9404163 A1 | 3/1994 |
| WO | 9702356 A1 | 1/1997 |
| WO | 9827829 A1 | 7/1998 |
| WO | 2004002495 A1 | 1/2004 |
| WO | 2006121803 A1 | 11/2006 |
| WO | 2007146416 A2 | 12/2007 |
| WO | 2008152207 A1 | 12/2008 |

OTHER PUBLICATIONS

Zhao et al. (2005) Inter. Immunopharma. 5: pp. 1436-1445.*
Krizkova et al. (2001) Mutation Research pp. 213-222.*
Nelson et al. (1984) Infect. Immun. 43(3): 1041-1046.*
International Search Report for PCT/FI2009/051017, Completed by the Swedish Patent Office on Mar. 31, 2010, 7 Pages.
Kath et al. "Mild enzymatic isolation of mannan and glucan from yeast *Saccharomyces cerevisiae*", Die Angewandte Makromolekulare Chemie 1999. vol. 268, No. 4667, p. 59-68.
Manners et al. "The Structure of a β-(1→3)-D-Glucan from Yeast Cell Walls", Biochem. J. 1973, vol. 135, p. 19-30.
Savolainen et al. "Allergen-induced in vitro expression of IL-18, SLAM and GATA-3 mRNA in PBMC during sublingual immunotherapy", Allergy 2007, vol. 62, p. 949-953.
Busetto et al. "A Single-Step, Sensitive Flow Cytofluorometric Assay for the Simultaneous Assessment of Membrane-Bound and Ingested Candida albicans in Phagocytosing Neutrophils", Cytometry Part A 2004, vol. 58A, p. 201-206.
Smith et al. "Diet-Induced Obese Mice Have Increased Mortality and Altered Immune Responses When Infected with Influenza Virus 1,2", The Journal of Nutrition 2007, vol. 137, p. 1236-1243.

* cited by examiner

*Primary Examiner* — Chris R Tate
*Assistant Examiner* — Russell Fiebig
(74) *Attorney, Agent, or Firm* — Brooks Kushman P.C.

(57) ABSTRACT

The present invention is directed to a method of production of an immunostimulatory composition having a saccharide fraction, the method including the steps of hydrolyzes of yeast cells and recovering the soluble fraction. The saccharide fraction having composition thus obtained may be incorporated as a food or beverage component or be used as a pharmaceutical for treatment of specific conditions.

18 Claims, 6 Drawing Sheets

PRODUCTION OF A SACCHARIDE COMPOSITION COMPRISING GLUCANS AND MANNANS BY ALKALINE AND ACID HYDROLYSIS OF YEAST CELLS

CROSS-REFERENCE TO RELATED APPLICATIONS

This application is the U.S. national phase of PCT Appln. No. PCT/FI2009/051017 filed Dec. 18, 2009 which claims priority to Finnish application 20080665 filed Dec. 18, 2008, the disclosures of which are incorporated in their entirety by reference herein.

The present invention is directed to a method of production of an immunostimulatory composition that comprises a saccharide fraction, the method comprising the steps of hydrolyses of yeast cells and recovering the soluble fraction. The saccharide fraction comprising composition thus obtained may be incorporated as a food or beverage component or be used as a pharmaceutical for treatment of specific conditions.

BACKGROUND OF THE INVENTION

Glucans, particularly beta (1-3)-glucans, have been very extensively studied, and have been shown to have a variety of pharmacological activities, including but not limited to anti-cholesterolaemic activity, hypoglycaemic activity, and stimulation of the immune system. For this reason beta-glucan comprising products have been used as feed additives in poultry, animal, fish or crustacean production. Glucans are insoluble polymers. The present invention reveals novel yeast derived materials comprising increased amounts of hydrolysed water soluble yeast carbohydrates and other soluble molecules.

The cell wall of Saccharomyces cerevisiae is primarily composed of beta-linked glucan, which is mainly a backbone of beta(1-3)-linked glucose units, with a minor component of inter and intra molecular branching via beta (1-6)-linkages. The yeast glucans in the prior art are mostly water insoluble polymers. The present invention reveals novel yeast derived materials comprising increased amounts of various water soluble hydrolysed yeast carbohydrates including specific polymer material comprising β6-linked glucose as major structure, and soluble α-mannose materials and other soluble molecules with specific molecular size.

The yeast derived material of prior art have been described to comprise mannans insoluble glycoproteins or possible as oligosaccharides. The present invention revealed novel α-mannose materials with specific molecular size mainly in low molecular weight polysaccharide range. The soluble α-mannose materials are in a preferred embodiment major carbohydrate component. The novel fractions further have useful characteristics including clearness, reduced taste and odor, especially when the yeast is produced from spent yeast from beer production.

Because of the very wide use of yeasts in the food and brewing industry, as well as in the production of industrial-grade alcohol, spent yeast cells are a major industrial by-product. Yeast-derived products themselves have considerable commercial value, for example in such products as yeast extracts, flavouring agents, flavour potentiators such as guanosine monophosphate and inosine monophosphate, and in the manufacture of enzymes, fine chemicals and products for use in the biochemical and pharmaceutical industries, such as trehalose, thymidine, nucleosides and nucleotides, etc. Waste yeast from the brewing industry is a major source of beta-glucans.

In addition, other species of yeast are also useful as a source of beta-glucans or mannose containing glycans, including but not limited to other yeast strains of Saccharomyces cerevisiae, other yeast using food or beverage fermentation processes such as other Saccharomyces species including e.g. Saccharomyces carlsbergiensis, Kluyveromyces fragilis, and Candida strains such as Candida utilis. All of these yeast strains can be produced using culture in food grade nutrients either by batch fermentation or continuous fermentation.

The purification of beta-glucans from yeast and other organisms has been extensively investigated, and a variety of methods is known. Most of these rely on the insolubility of beta (1-3)-glucan in alkali or in organic solvents. The principal known methods are:
(a) High temperature extraction with concentrated sodium hydroxide, followed by high temperature extraction with acid and precipitation with ethanol (e.g. Manners, D. J. et al., Biochem. J. 135 19-30 (1973), Jamas, S. et al., U.S. Pat. Nos. 4,810,646, 5,028,703, and 5,250,436). Many of these protocols require preliminary homogenisation of the yeast cells, and many require multiple repetition of each extraction step.
(b) Extraction with concentrated sodium hydroxide, followed by high temperature acid extraction and enzyme treatment to modify or purify the glucan (see for example Czech Patent Application No. 890038 by Masler, L. et al. which reports purification of beta-D-glucan by alkali-acid extraction, followed by treatment with enzymes having amylase activity).
(c) Extraction of yeast cell wall preparations resulting from autolysis or enzyme degradation of yeast with concentrated phenol:water (1:1) (see for example U.S. Pat. No. 4,138,479 by Truscheit, E. et al.).
(d) Extraction with organic solvents such as isopropanol, ethanol, acetone, or methanol either alone or in the presence of alkali (see for example Japanese Patent publications No. 7051081, 6340701, 5295003, and 3002202; European Patent Application No. 515216).

Acid treatment is known to reduce the number of beta (1-6)-linkages in the glucan material and this results in an increase in viscosity.

The cell wall of yeast is mainly composed of:
(i) fibrillar, alkali insoluble beta (1-3)-linked glucan, with side branches of beta (1-6)-linked glucan.
(ii) alkali-soluble beta (1-3)-linked glucan with side branches of beta (1-6)-linked glucan.
(iii) amorphous acid-soluble beta (1-6)-glucan, with intermittent beta (1-3)-linkages.
(iv) amorphous alkali-soluble mannan linked to proteins.

Existing methods to isolate the beta-glucans commonly use a multi-step alkali-acid extraction process. The alkali extraction steps remove most of the amorphous mannoprotein and glucan material, and the subsequent acid extraction steps remove the glycogen and most of the beta (1-6)-side branches from the fibrillar predominantly beta (1-3) linked glucan. A final solvent extraction step is sometimes used to remove lipids.

The glucan methods involve strong alkaline extraction and optionally weak acid treatment to obtain insoluble mainly beta3-linked glucans. The present invention includes more effective acid hydrolysis preferably in elevated temperatures to produce more soluble material and an alkaline hydrolysis to improve the solubilization, the alkaline reaction is used to extract alkali soluble material but the soluble fraction is not discarded but retained. The present invention further comprise separation and/or fractionation steps to remove insoluble material likely including β3-glucan, and optionally recycling the insoluble material to hydrolysis step to produce more soluble carbohydrates, and to remove low molecular weight materials such as monosaccharides or low molecular weight oligosaccharides or practically all oligosaccharides and removing salts. It is realized that acid and alkaline treatments produce salts.

It is clear that, given the retail price of glucan for some applications, the cost of producing glucan using existing published or patented methods is not commercially viable. These methods have at least one major disadvantage, they are aimed at only producing the fibrillar, alkali-insoluble form of glucan. Other forms of glucan and the mannan present in the cell wall are removed as by-products of the process. These represent an additional amount of glucan, which could have significantly increased the glucan yield, and which may be functionally important. In addition, after or between hydrolysis treatments soluble components are discarded whereas insoluble, mostly beta(1-3)glucan is retained. The method of production of present invention can be used to produce a soluble β6-glucose linkage structure comprising carbohydrate or saccharide materials for, used in or as immunostimulatory and/or modulatory compositions. The increased solubility and the reduction of the amount of β3-glucans structures distinguishes present soluble materials from known β-glucose containing materials.

Mannan is a polymer composed of mannose units. In yeasts, mannan is associated with protein in both the external surface of the yeast cell wall, as a muscigenous polysaccharide, and in the inner cell membrane. It generally accounts for about 20-50% of the dry weight of the cell wall. Mannan is linked to a core-peptide chain as an oligomer or polymer. The complex contains about 5-50% proteins. Oligomeric mannan is bonded directly to serine and threonine, whereas polymeric mannan is bonded to asparagine via N-acetylglucosamine. In the manno-protein complex, the mannose units are linked by .alpha.-1,6, .alpha.-1,2 and .alpha.-1,3-linkages. The present invention produced concentrated soluble mannans and mannose glycans, which have useful biological activities and distinct characteristics in NMR analysis.

Mannan-oligosaccharides (MOS) have suggested to be released from yeast cell walls by proteolytic action. Proteolysis produced mannan may have high molecular weight, contain allergenic proteins and likely have large molecular weight and poor solubility. Such released MOS type products have limited usefulness. In a specific embodiment the present method may include additional enzymatic and proteolytic steps. It is realized that the present methods the alkaline hydrolysis beta-eliminates O-linked and/or N-linked mannose glycopeptides. It further realized that the peptide materials may have negative effects of the product structure and even have negative immunological.

More soluble and useful mannans according to the present invention effectively bind to bacterial pathogens of the intestinal tract and block their ability to colonize the intestinal tract. For example, *E. coli, Salmonella* spp. and *Vibrio cholera* have proteins on their surface (lectins) which bind to the mannose sugar residues of the mannans. The present invention revealed novel active saccharide compositions comprising majority of glycans with molecular weight larger than oligosaccharide and capable of polyvalent and oligovalent presentation of oligosaccharide epitopes. The present method further produced high amounts of useful terminal oligosaccharide sequences for pathogen binding. The usefulness of oligovalent and polyvalent carbohydrate epitopes for antiadhesion therapies and treatments against infections or for interactions with cell surface lectin receptors is well-known in the art and frequently reviewed e.g. by K-A. Karlsson and in Nathan Sharon's publication since Beachey 1981 (Beachey, E. H. (1981) *J. Infect. Dis.* 143, 325-345). The polyvalent glycans are used for anti-adhesion for preventing the binding of pathogens to patients tissue. By definition oligosaccharide contains less than 10 monosaccharide residues, Mw less than 1700, while present material comprise major amount of carbohydrates larger than about 5000 Da. The present materials are useful against the pathogens and harmful microbes because of the high valency improving binding and solubility of the novel mannose glycans.

There is a clear need in the art for a rapid and inexpensive method of saccharide fraction extraction, which avoids loss of alkali soluble glucans and mannans, which has improved recovery of glucans and mannans and which results in a biologically active preparation.

We have now surprisingly found that soluble immunostimulatory composition that contains saccharide fraction can be isolated using a simple two-hydrolysis steps involving procedure and that excellent yields of a soluble product with high immunostimulatory activity is obtained. Hydrolysis may be supplemented by treatment with enzymes or other agents or mechanical, pneumatic or hydrostatic treatment or with heat and if desired, the properties of the saccharide fraction can be modified by acid treatment, degree of homogenisation or by varying the type of enzyme used.

SUMMARY OF THE INVENTION

Figure 1:
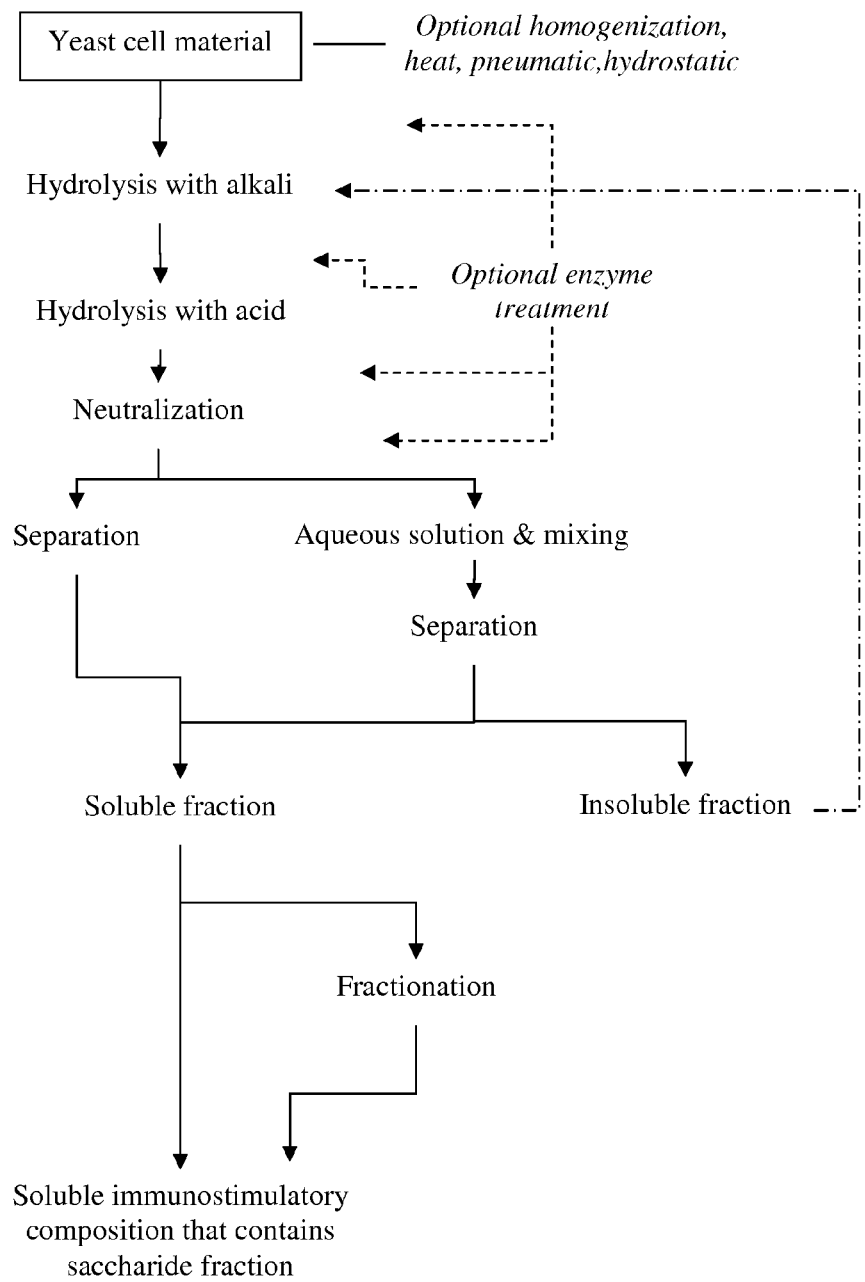
FIG. 1. A flowchart of one embodiment of a process for production of soluble immunostimulatory composition that contains saccharide fraction in accordance with the present invention.

The invention is directed to a method of production of a soluble immunostimulatory composition that contains saccharide fraction, comprising the steps of:
  a. providing yeast cell material,
  b. subjecting yeast cell material to hydrolysis steps with an alkali and an acid to release mannans and glucans from yeast cell material, and optionally neutralising the obtained material and/or optionally desalting the material
  c. separating soluble and insoluble fraction from the material obtained in step ii), and, optionally,
  d. subjecting the soluble fraction of step iii) to further fractionation step,
  wherein soluble fraction comprises mannans and beta-1,6 glucans, and wherein soluble fraction is substantially odourless and tasteless.

Preferably, the invention is directed to the method, wherein yeast cell material is first treated with an acid.

Preferably, the invention is directed to the method, wherein material obtained in step ii) is further contacted with an aqueous solution and preferably mixed in said aqueous solution.

Preferably, the invention is directed to the method, wherein yeast cell material is about 5% to 50%, 10% to 30%, preferably from 15% to 25%, more preferably from 17% to 23%, even more preferably 19% to 21% and most preferably about 20% of dry content.

Preferably, the invention is directed to the method, wherein saccharide fraction comprises less than 0.1% w/w of beta-1,3 glucan of dry matter or is essentially devoid of beta-1,3 glucan, or the amount of beta-1,3 glycan is less than 30% of the amount of β1,6 glucan.

Preferably, the invention is directed to the method, wherein mannans and/or have a molecular weight of at least 1,000 Da or have been obtained by removal of fraction separable ultrafiltration with membrane with cut-off of at least 500 Da.

Preferably, the invention is directed to the ultrafiltration method, wherein the cut-off the membrane is at least 1000 Da or 3000 Da.

Preferably, the invention is directed to the method, wherein soluble fraction of step iv) is concentrated.

Preferably, the invention is directed to the method wherein concentration is performed with ultrafiltration.

Preferably, the invention is directed to the method, wherein the alkali hydrolysis is performed at a pH of about 9 to about 13, preferably between about 11 to 13, and more preferably between about 12 and 13.

Preferably, the invention is directed to the method, wherein the acid hydrolysis is performed at a pH of about 1 to 4, preferably at a pH about 2 to about 3.

The invention is directed to the method of production of a soluble immunostimulatory composition that contains saccharide fraction, comprising the steps of:
  i) providing yeast cell material,
  ii) subjecting yeast cell material to a hydrolysis with an alkali at a pH about 9 to 13 and a temperature of about 10° to 90° C. for about 10 min to 8 hours and an acid at a pH about 2 to 3 and a temperature of about 30° to 90° C. for about 3 to 48 hours, neutralising the material, optionally contacting the material with an aqueous solution,
  iii) separating soluble fraction from the material obtained,
  iv) subjecting the soluble fraction of step iii) to fractionation with ultrafiltration, and
  v) reducing the ultrafiltrated fraction to a solid material.

Preferably, the invention is directed to the method, wherein the soluble saccharide fraction is fractionated, isolated, separated or purified from the soluble fraction. In a preferred embodiment these are referred as further purification.

Preferably, the invention is directed to the method, wherein fractionation, isolation, separation or purification is performed by a method or any combinations of methods selected from the group consisting of
  a chromatographic method selected from the group consisting of chromatography for absorption of charged and or lipophilic (hydrophobic) impurities, size exclusion chromatography, affinity chromatography with matrix binding to the saccharides and/or
  a phase separation solution method and/or
  centrifugation.

The invention is directed to a soluble saccharide fraction obtained according to the methods of invention, optionally including further purification steps and a soluble immunostimulatory composition that contains saccharide fraction obtained according to the methods.

The invention is directed a soluble immunostimulatory composition that contains saccharide fraction and wherein saccharide fraction comprises mannans and beta-1,6 glucans and less than 1% of beta-1,3 glucan of dry matter, and preferably the amount of β3-glucans is less than 50% of the β3-glucans, and wherein the composition is substantially odourless and tasteless.

The invention is directed the soluble immunostimulatory composition, wherein said composition comprises 0.001-10%, more preferably 0.005-5%, even more preferably 0.01-3%, and even most preferably 0.01-1.5% β1-6 glucan of the dry weight.

The invention is directed the soluble immunostimulatory composition, wherein said composition comprises mannan 1-50%, more preferably 2-50%, even more preferably 3-50%, even more preferably 4-50%, even more preferably 4-40%, even more preferably 5-35%, most preferably 5-25% or 10-20% w/w of the dry weight.

The invention is directed the soluble immunostimulatory composition, wherein said composition comprise mannans: glucans in ratio as 14:0.32 or higher than 40:1 or β6-glucan or β-glucans or, preferably less than 20% w/w, more preferably less than 10% w/w, more preferably less than 5% w/w, more preferably less than 4%, even more preferably less than 3.5%, even more preferably less than 2.5%, most preferably less than 2.3% of the mannans on dry weight basis.

The invention is directed the soluble immunostimulatory composition, wherein said composition comprise an amount of the soluble β-glucan and mannan of at least about 14% w/w, more preferably at least about 15% w/w, more preferably at least about 22% w/w of the dry weight of the composition.

The invention is directed the soluble immunostimulatory composition, wherein the mannans and glucans have a molecular weight of at least 500 Da, more preferably at least 1000 Da.

The invention is directed the soluble immunostimulatory composition, wherein the composition comprises major part of glucan and mannan saccharide materials eluting between void volume and position of hexose polysaccharide Mw marker of 5000 Da, and optionally a minor portion of the material eluting between Mw markers of 1000 and 5000 Da, when the Mw marker of 5000 elutes at about 10.5 min, and the Mw marker of about 15.8 min from Superdex Peptide 10/300 GL column with total elution volume of 18 ml and column length 30 cm and when the carbohydrates are analyzed as reducing end diaminobenzamide labeled structures.

The invention is directed the soluble immunostimulatory composition, wherein the composition comprises about 80 mol % of materials larger than 5000 Da and about 20 mol % of materials eluting between Mw markers of 1000 and 5000 Da.

The invention is directed the soluble immunostimulatory composition, wherein the composition comprises at least about 91% (w/w) of soluble mannan materials larger than 5000 Da, more preferably at least 95% w/w.

It is realized that composition comprising soluble, especially solubility as 1% water solution, polymeric α-mannose saccharides referred as mannans are not well known. The polymers are typically larger than 10-mer, which is limit of oligosaccharides such as "MOS" products. The invention further revealed novel soluble polymeric 6-glucans and their concentrated compositions with mannans.

The inventors have a previous PCT application describing optimized acid soluted yeast products, in comparison to these, the present invention revealed materials with higher saccharide content of mannans and β6-glucans above 14%, or even larger, while previous application had about 2% mannose materials. To allow more accurate quantitation by same method, previous acid hydrolysis products were compared by NMR in FIG. 3 and EXAMPLE 2 showing that the prior material contained only about 12% of the mannose materials of present invention. Furthermore, when prior material contained at least 10% mannose oligosaccharides, the present material contains in preferred fractions practically no oligosaccharides. Thus the amount of most useful polyvalent mannan was increased about 10 fold by the new process including base/alkaline hydrolysis. The invention further revealed higher mannan amount increased similarly relative mannan β6-glucan ratio and thus changing the composition.

While spent yeast from the fermentation industry is especially useful in the process of the invention, it will be clearly understood that the invention is applicable to any source, such as other yeasts used in the food and fermentation industries. These include but are not limited to yeasts used in the production of viscosity-imparting agents, emulsifiers, fibers, films, coating substances, supports for affinity chromatography and gel electrophoresis, in cell culture media, as filter pads and in cement. They are also widely used as food thickeners and as a source of dietary fibre, and as carriers and coating agents in pharmaceutical products. The present invention is directed to yeasts derived from fermentation processes for human food or beverage production. Preferred types of yeast includes alcohol industry derived yeasts, in a preferred embodiment brewery derived yeast and/or vine industry derived yeasts, in another preferred embodiment derived from yeast residue/spent yeast from a beer production process.

The term "yeast" means here cultivable eukaryotic microbe which has carbohydrates useful for production of an immunostimulatory glycan/saccharide composition by methods according to the invention, in a preferred embodiment the yeast is a fungus species.

The person skilled in the art will readily be able to determine the most suitable conditions under which the process of the invention can be applied to other yeast species.

The person skilled in the art will be aware that for some applications of soluble immunostimulatory composition that contains saccharide fraction produced using the method of the invention is advantageously provided in a dry form. The preparation is suitably dried by any suitable process, including but not limited to freeze-drying, roller drum drying, oven-drying, spray-drying, ring-drying or dried using film-forming equipment, and either may be used without further processing, or may be milled using any suitable technique to a particle size preferably of less than 20 micron. For other applications, a wet product such as a viscous paste, is suitable, and the preparation can be used either without further processing or following mechanical disruption to increase its viscosity and to reduce particle size.

According to an aspect, the invention provides a soluble immunostimulatory composition that contains saccharide fraction produced by the process of the invention. The soluble immunostimulatory composition that, in dry form, contains saccharide fraction according to the invention preferably comprises β1-6 glucan (for example 0.001-10%, more preferably 0.005-5% and most preferably 0.01-3%, and most preferably 0.01-1.5% of the dry weight) and mannan (for example, 1-50%, more preferably 2-50%, even more preferably 3-50%, even more preferably 4-50%, even more preferably 4-40%, even more preferably 5-35%, and most preferably 5-25% of the dry weight, even more preferably between 10-20% w/w), preferably in water soluble form with the NMR characteristics according to the invention.

The preparation or composition may preferably comprise of beta 1-6, and 1-4, more preferably beta 1-6 glucan and mannans and less than 8%, or preferably essentially is devoid of, beta 1-3 glucans or contain minor amount of beta 1-3 glucans. The composition comprises preferably less than 50% of beta 1-6 glucan of the amount of β3glucan, more preferably less than 30% of beta 1-6 glucan of the amount of β3glucan, even more preferably less than 25% of beta 1-6 glucan, preferably from 5 to 25% of β6-glucan of the amount of β3glucan. In a preferred embodiment the amounts of the saccharides is analyzed by integrating signal of NMR spectrum.

The soluble immunostimulatory composition that contains saccharide fraction may be used alone. However, most commonly it will be provided in conjunction with other components.

Thus, in an aspect of the invention, preferred embodiments include but are not limited to a compositions for nutrition or therapy, preferably including e.g. food composition, food supplement compositions, diet food compositions, pharmaceutical composition including prescription and OTC-drug compositions, clinical nutrition compositions, topical medicine compositions, natural medicine compositions, nutraceutical composition and nutraceutical additives. The compositions are aimed for the use by subject or patient in the need of the composition, preferably by human or animal, and most preferably by a human subject.

The invention is further directed to use of the novel saccharide fractions in methods for production of pharmaceutical and/or therapeutic and/or nutraceutical compositions, preferably when the compositions are aimed for the use for subject or patient in the need of immunomodulation or immunostimulation or anti-infectious treatment.

Thus, in this aspect of the invention, preferred embodiments further include but are not limited to a pet animal preferably cat or dog, cattle, pig, poultry, fish, crustacean or shellfish feed composition comprising the soluble immunostimulatory and anti-infective composition that contains saccharide fraction of the invention, together with one or more veterinarily acceptable food components; a soluble immunostimulatory composition that contains saccharide fraction of the invention together with a pharmaceutically acceptable carrier; a pharmaceutical composition comprising a pharmaceutically active agent and the soluble immunostimulatory composition that contains saccharide fraction of the invention as either a carrier or an adjuvant or as a coating for a solid dosage for such as a tablet or capsule. The soluble immunostimulatory composition that contains saccharide fraction can also be supplied in drinking water to cattle, pet, poultry or animals, or in ambient water to fish, crustaceans or shellfish.

Other embodiments of the invention include animal feeds, food supplements, pharmaceuticals, and nutraceuticals that comprise soluble immunostimulatory composition that contains saccharide fraction made by methods of the invention.

It will be clearly understood that the composition of the invention is generally suitable for use in products for which beta-glucans and mannans are known to be useful. In same cases further purification may be desirable or necessary, and if so purification steps known per se may be used.

DETAILED DESCRIPTION OF THE INVENTION

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

By the term "immunostimulatory composition that contains saccharide fraction" as used herein is meant an immunostimulatory composition that contain saccharide fraction which stimulates (e.g. has a mitogenic effect on, or induces or increases cytokine expression by a vertebrate lymphocyte and/or other activates white blood cell especially macrophages.

By the term "saccharide fraction" as used herein is meant a soluble fraction obtained by the methods of the present invention and which contains carbohydrates, oligosaccharides and other sugar molecules derived from the yeast cell materials of the invention.

As used herein and in the appended claims, a "taste" shall mean any taste which is salty, bitter, sweet, sour, alkaline, umami, astringent, tangy, dry, sharp, cool, hot, burning, acidic, spicy, pungent and/or metallic. Such taste shall include any and all taste(s) as well as any and all aftertaste(s). Once again this list is not all inclusive as one skilled in the art would recognize.

By the term "substantially tasteless" as used herein is meant a compound or composition that has substantially no taste upon initial ingestion.

By the term "substantially odorless" as used herein is meant a compound or composition that has substantially no odor upon initial nasal exposure or inhalation through a nose.

The substance or pharmaceutical composition according to the invention may be administered in any suitable way, although it is preferable to use oral administration.

The term "treatment" used herein relates to both treatment in order to cure or alleviate a disease or a condition, and to treatment in order to prevent the development of a disease or a condition, also referred as prophylactic treatment. In a preferred embodiment the prophylactic treatment prophylactic treatment by anti-adhesion reducing pathogen load, in an another preferred embodiment the prophylactic treatment is an immunomodulatory treatment with increase of a cytokine or chemokine expression. The treatment may either be performed in an acute or in a chronic way.

The term "patient", as it is used herein, relates to any human or non-human mammal in need of treatment according to the invention.

The carbohydrate nomenclature follows essentially the recommendations by the IUPAC-IUB Commission on Biochemical Nomenclature. Linkages are indicated with anomer structure and linkage positions or shortened versions e.g. beta-1,3, beta(1,3) or beta1-3, or β1-3 or β3 meaning the same for the structures according to the invention. It is assumed that Glc (glucose), Man (mannose), Gal, GlcNAc, GalNAc, NeuAc and NeuGc are of the D-configuration, Fuc of the L-configuration, and all sugars present in the pyranose form.

According to the invention it is possible incorporate the substance according to the invention, optionally together with a carrier, in a pharmaceutical composition suitable for treatment of a condition due to the presence of pathogen such as a virus or bacterium, in patient, in a preferred embodiment in the gastrointestinal tract or in respiratory tract of a patient or to use the substance according to the invention in a method for treatment of such a condition. Examples of conditions treatable according to the invention are infectious diseases and diarrheas.

The pharmaceutical composition according to the invention may also comprise other substances, such as an inert vehicle, or pharmaceutical acceptable adjuvants, carriers, preservatives etc., which are well known to persons skilled in the art.

Furthermore, the substance according to the present invention may be administered together with other drugs or therapeutic substances or compositions preferably aimed for immunostimulation and/or anti-adhesion therapy.

Furthermore, it is possible to use the substance according to the invention in order to identify one or more adhesins by screening for sequences that binds to the substance according to the invention. Said sequences may be, e.g., proteins or carbohydrates. The carbohydrate binding protein may be a lectin or a carbohydrate binding enzyme. The screening can be done for example by affinity chromatography or affinity cross linking methods.

Anti-Infective Treatments by Anti-Adhesion

More soluble and useful mannans according to the present invention effectively bind to bacterial pathogens of the intestinal tract and block their ability to colonize the intestinal tract. For example, E. coli, Salmonella spp. and Vibrio cholera have proteins on their surface (lectins) which bind to the mannose sugar residues of the mannans. Part of the inventors have shown that human gastrointestinal tract contain receptors for the mannose binding diarrhea causing pathogens such as diarrhea causing E. coli, which also have receptors binding mannose glycans, especially Manα3Man comprising structures (PCT FI2003/00528). The present invention revealed novel active saccharide compositions comprising majority of glycans with molecular weight larger than oligosaccharide and capable of polyvalent and oligovalent presentation of oligosaccharide epitopes. The present method further produced high amounts of useful terminal oligosaccharide sequences for pathogen binding. The usefulness of oligovalent and polyvalent carbohydrate epitopes for anti-adhesion therapies and treatments against infections or for interactions with cell surface lectin receptors is well-known in the art and frequently reviewed e.g. by K-A. Karlsson and in Nathan Sharon's publication since Beachey 1981 (Beachey, E. H. (1981) J. Infect. Dis. 143, 325-345). The polyvalent glycans are used for anti-adhesion for preventing the binding of pathogens to patients tissue. Adhesion of microorganisms is a first step in pathogenesis of infections, where the specificity of the adhesins of the infectious agent, and the receptor structures, such as glycans structures expressed by the epithelial cells of the host target organ are important determinants of the host range and the tissue tropism of the pathogen. In order to treat a disease or a condition due to the presence of pathogen in the gastrointestinal tract of a patient it is possible to use the substance according to the invention for anti-adhesion, i.e. to inhibit the binding of pathogen to the receptors in the intestinal epithelium of the patient. When the substance or pharmaceutical composition according to the invention is administered it will compete with the receptor in the binding of the bacteria, and all or some of the bacteria present in the gastrointestinal tract will then bind to the substance according to the invention instead of to the receptor on the gastric epithelium. The bacteria will then pass through the intestines and out of the patient attached to the substance according to the invention, resulting in a reduced effect of the bacteria on the patient's health.

According to the invention it is possible to treat diseases due to the presence of diarrheagenic pathogens, especially diarrheas by anti-adhesion and immunostimulation.

Treatment by Immunostimulation

The present invention is directed to immunostimulation treatments preferably in order to stimulate immune system for protection against pathogens. In a preferred embodiment this immunostimulation is aimed for inducing white blood cells such as macrophages against pathogenic microbes such as viruses, bacteria and/or fungi. In another preferred embodiment the immunostimulation is used for balancing immune reactions to prevent harmful conditions such as autoimmune and/or allergic conditions. The balancing of immunostimulation is typically directed to activation and inactivation of specific T-helper lymphocyte cell populations. The immunostimulation is in a preferred embodiment mediated by specific factor including chemokine or cytokine molecules such as interleukin and/or interferon and effect of immunostimulation may be measured as a change of the factor(s) and/or as anti-microbial effect of the white blood cells.

As used herein, the term "composition" means a composition that can be administered to a human that is orally ingested by the human, bars, pills, capsules, administered to companion animal that is orally ingested by a companion animal, supplements for a companion animal, pet food, dog food, cat food, treats, biscuits, raw hide, treats, chews, fillers, gravy, sauce, beverage, supplemental water, and combinations thereof. The composition can be wet, moist, and/or dry.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

Suitable yeast species, to be used as yeast cell material, of the present invention include, but are not limited to, yeast strains of *Saccharomyces* species and of *Saccharomyces cerevisiae* (including baker's yeast strains and brewer's yeast strains), *Kluyveromyces fragilis*, and *Candida* strains, such as *Candida utilis*, and combinations thereof. Other strains of yeast, for and used as yeast cell material, which are suitable sources of soluble immunostimulatory composition that contains saccharide fraction include preferably food grade yeast species such as *Saccharomyces delbruekii, Saccharomyces rosei, Saccharomyces microellipsodes, Saccharomyces carlsbergensis, Schizosaccharomyces pombe, Kluyveromyces lactis, Kluyveromyces polysporus, Candida albicans, Candida cloacae, Candida tropicalis, Candida guilliermondii, Hansenula wingei, Hansenula arni, Hansenula henricii, Hansenula Americana* and combinations thereof. These yeast strains can be produced using culture in food grade nutrients either by batch fermentation or continuous fermentation.

Specifically, the process in accordance with the present invention relates to a method of production of a soluble immunostimulatory composition that contains saccharide fraction. In an exemplified embodiment, the method or production or process includes a first step of providing yeast cell material, e.g., brewer's yeast, (typically a 5% to 50%, 5% to 40%, 10% to 30%, particularly a 15% to 25%, and more particularly a 17% to 23% or 19% to 21% of dry content, most preferably about 20% of dry content), followed by subjecting yeast cell material to hydrolysis steps with an alkali and an acid to release mannans and glucans from yeas cell material.

In a preferred embodiment brewer's yeast or brewer's yeast cream is used. Such yeast material includes plant derived non-soluble materials, especially plant derived non-soluble materials comprising plant polysaccharides such as hemicellulose saccharides and plant derived β-glucan materials such as cereal beta glucans, preferably the cereal is cereal used in brewing process, most preferably barley. In another preferred embodiment the material produced from the brewer's yeast comprise major amounts of brewer's yeast materials and is devoid of or comprises only minor amount of plant carbohydrates. In another preferred embodiment any yeast fermented with a plant based or plant derived materials is suitable for the use as yeast cell material.

Reaction Conditions of Alkali and Acid Hydrolysis

The invention is directed to alkali reaction capable of improving the taste and odor of the soluble product, preferably when the alkali hydrolysis is performed in combination with the acid hydrolysis. The invention is further directed to the combination of alkali and acid hydrolysis, when the alkali treatment is capable of improving the amount of soluble mannans, in a preferred embodiment by causing release of N-linked glycans by an elimination reaction and/or releasing O-linked glycans by beta elimination reaction.

These reaction reduce the peptides/proteins bound to glycans and improve the quality of the product. It is known that the glycan peptide linkages can be cleaved by various bases e.g. by about 0.1-0.2 M NaOH and incubation of several hours to about 48 hours, or at an elevated temperature such as about 50-70 degrees of Celsius for about 0.5 to 8 hours, preferably about 2-8 hours at 50-60 degrees of Celsius, which are preferred conditions assuming adjusting pH to corresponding value of about 13 because of buffering capacity of the yeast material.

The hydrolysis with an alkali may suitably be carried out at a pH of at least 9, at least 9.5, particularly at least 9.7, and more particularly at least 10, more particularly at least 10.5, and more particularly at least 11.5. The hydrolysis with an alkali may suitably be carried out at a pH about 11 to about 14, preferably at a pH about 12 to about 13, most preferably at a pH about 12.5. The hydrolysis with an alkali may suitably be carried out at a pH between about 9.0 and 11 or pH between about 11.0 and 13 or pH between about 9.0 and 13.

Preferred alkali reagent for the hydrolysis is sodium hydroxide, other food acceptable alkali material may be used such as other alkali metal hydroxides especially potassium hydroxide KOH, or earth alkali hydroxides preferably $Ca(OH)_2$ or $Mg(OH)_2$ or mixtures thereof, or carbonates such as sodium $(Na)_2CO_3$ or potassium $(K)_2CO_3$ or calcium carbonate $CaCO_3$, or in a specific embodiment ammonia $NH_3$. Sodium containing alkali reagents are preferred for brewery yeast materials. In a specific embodiment the process includes production of phosphate ions such as acid hydrolysis by phosphoric acid and further includes step where it is desalted, and/or neutralized and/or alkaline hydrolyzed by and alkali precipitating the salt such as $Ca(OH)_2$ precipitating phosphates as $Ca^{2+}$ phosphates. The precipitation desalting step may be performed in context of the separation step, separating the precipitated phosphate salt and the insoluble material, or before the fractionating step.

The hydrolysis with an acid may suitably be carried out at a pH of less than 4.5, particularly less than 3.5, and even more particularly less than 2.5. The hydrolysis with an acid may suitably be carried out at a pH about 1 to 4, preferably at a pH about 2 to about 3, more preferably at pH between about 2.1 and 2.8, more preferably at pH between about 2.2 and 2.7, most preferably at a pH about 2.3, 2.4, or 2.5.

The temperature for carrying out the hydrolysis, preferably both alkali and acid, may suitably be at least preferably carried out at elevated temperatures preferably being at least 30° C., even more preferably 40° C., even more preferably at least 45° C., at least 50° C., particularly at least 60° C., more particularly at least 70° C., and even more particularly at least 75° C.

In a preferred embodiment the alkali hydrolysis steps are performed in temperatures from 0° C. to 100° C., more preferably in lower temperature range from 0° C. to 60° C., and even more preferably from 10° C. to about 90° C., and in a preferred embodiment from 10° C. to about 50° C. Temperatures close to 50° C., from 30° C. to 65° C., more preferably 40° C. to 55° C., and even more preferably 45° C. to 55° C. are especially preferred for alkaline hydrolysis, especially in context of brewers yeast and sodium hydroxide.

The hydrolysis reactions may be performed with reaction times from a few minutes, e.g 5 min especially for the alkaline hydrolysis to several days for the acid hydrolysis.

The acid hydrolysis is in a preferred embodiment be carried out for at least 2 hours, particularly for at least 3 hours, more particularly for at least 5 hours, particularly at least 6 hours, and more particularly at least 7 to 8 hours, and even more particularly for at least 8-24 hours. The hydrolysis may suitably be carried out for less than 48 hours, more preferably less than 32 hours or more preferably in less than 24 hours, more preferably less than 12 hours, particularly less than 10 hours, and even more particularly less than 9 hours. The hydrolysis in a preferred embodiment be carried out for 2 to 6 hours, preferably for 3 to 5 hours and most preferably about 4 hours.

The acid hydrolysis is preferably performed and an acid at a pH about 2 to 3 and a temperature of about 30° to 90° C. for about 2 to 48 hours.

The alkaline hydrolysis is in a preferred embodiment be carried out for at least 1 minute, more preferably at least 5 minutes, more preferably at least 10 minutes, more preferably at least 30 minutes, more preferably from at least at least about 10 minutes to 1 hour, more preferably from 15 minutes to 45 minutes, 20 minutes to about 40 minutes or about 30 minutes.

In another preferred embodiment the reaction time is increased and lower temperature and/or alkaline concentration is used and the reaction lasts at least 1 hour, more preferably at least 1.5 hours, more particularly for at least 2 hours, more particularly for at least 3 hours, particularly at least 4 hours, and more particularly at least 5 to 8 hours, and even more particularly for at least 1-4 hours or at least 1-8 hours. The hydrolysis may suitably be carried out for less than 48 hours, more preferably less than 24 hours, more preferably, less than 12 hours, particularly less than 10 hours, and even more particularly less than 9 hours. The hydrolysis in a preferred embodiment be carried out for 1 to 6 hours, preferably for 1 to 5 hours and most preferably about 1-3 hours.

It is realized that higher temperature such as 55° C. or more may increase caramellization reactions, and are less favored to certain products, product with requirement of less colored caramellization products are preferably performed with lower temperatures with longer reaction times.

The hydrolysis with alkali may suitably be carried out for at least 10 min, 30 min, 1 hour, particularly at least 2 hours, and at least 3, 4, 5, 6, 7 or 8 hours. The hydrolysis may suitably be carried out for less than 12 hours, particularly less than 10 hours, and even more particularly less than 9, 8, 7, 6, 5, 4, or 3 hours. The hydrolysis with an acid may suitably be carried out for 1 to 8 hours, 2 to 6 hours, preferably for 3 to 5 hours and most preferably about 4 hours. The hydrolysis with an acid may suitably be carried out for at least 30 min, 1 hour, particularly at least 2 hours, and at least 3, 4, 5, 6, 7 or to 8 hours.

In a preferred embodiment alkaline hydrolysis is performed by subjecting yeast cell material to a hydrolysis with an alkali at a pH about 9 to 13 and a temperature of about 10° to 90° C. for about 10 min to 8 hours.

Preferred Concentration of Acid in the Reaction

The present invention is directed to the use of minimum amount of the acid and base. The preferred final concentrations of the acid in the process depends on the amount of dry material in the reaction mixture. In a preferred embodiment the amount of yeast raw material as dry material is about 5-70%, more preferably 5-50%, more preferably 5-30% even more preferably 10-25%, even more preferably 15-25% or about 20%. It is realized that preferably concentrated spent yeast from fermentation process such as spent brewery yeast is used with concentration comprising preferred amount of yeast dry weight such as about 20% of dry weight. In another embodiment in medium concentrated as about 30% of dry weight, or in another embodiment in highly concentrated as about 40% of dry weight. The preferred medium range concentrations are from 20 to 40% of dry weight, more preferably from 22 to 38%, more preferably from 25 to 35%, even more preferably from 27 to 33% of dry weight. The preferred high range concentrations are from 30 to 60% dry weight, even more preferably from 30 to 50% of dry weight, even more preferably from 32 to 48%, even more preferably from 35 to 45%. In a preferred embodiment the present process includes a preferred acid and alkaline hydrolysis and a preferred concentration of yeast dry material is used, more preferably medium or high range concentrations or with any combinations thereof. The high concentrations are preferred to improve process effectively and energy efficiency.

It is realized that optimal effect of acid is obtained by adjusting the pH of the yeast material by adding concentrated acid and or base to the yeast material. The concentrated acid or base may have concentration from 0.1 to 10 M, preferably from 0.5 M to about 8 M. The concentration of the acid or base is several or order of magnitude more than the desired administered acid concentration per the reaction volume.

The present invention is directed to optimized low acid amounts from about 0.1 to 0.75 M, more preferably 0.1-0.5 M, and higher acid amounts from about to be used with concentrated raw material or at lower pH ranges (e.g. pH 0.5-1.5), with higher concentration from about 0.5 M to 1.5 M, more preferably from 0.75 M to 1.25 M. In a preferred embodiment the low acid amounts and fosforic acid is used. It is realized that with the higher administered concentrations per volume in the reaction (final concentration) from about 0.3 M to about 2.0 M, more preferably from about 0.3 M to about 1.5 M, preferably from about 0.5 to about 1.5 M, or from 0.75 M to 1.25 M higher amounts are preferred to obtain higher solubilization of the preferred glycans.

Preferred final concentrations administered for preferred strong inorganic acids; hydrochloric acid, sulphuric acid or fosforic acid ($H_3PO_4$); are from about 0.3 M to about 2.0 M, more preferably from about 0.3 M to about 1.5 M, preferably from about 0.5 to about 1.5 M, or from 0.75 M to 1.25 M and higher solubilization of the glycans is obtained, when the reaction is performed at temperature about 80 degrees of Celsius (preferably between 70-100 degrees of Celsius, even more preferably between 70 and 95 degrees of Celsius even more preferably between 75 and 85 degrees of Celsius. The preferred reaction time is about 4 hours, preferably from 2 to 8 hours, more preferably 3 to 5 hours, most preferably from 3.5 to 4.5 hours. In a preferred embodiment the final concentration range is used to adjust the pH to preferred value preferably between pH 1.5-4.0, more preferably between 2.0 and 3.5, even more preferably between 2.0 and 3.0.

The alkaline is preferably administered to obtain preferred pH. The administered alkaline concentration per reaction volume is preferably from about 0.01 M to about 10 M, more preferably from about 0.050 M to about 5.0 M, more preferably from about 0.05 M to about 4.0 M.

Preferred acids include inorganic acids such as fosforic acid ($H_3PO_4$), hydrochloric acid and sulphuric acid. In a preferred embodiment the acid is fosforic acid ($H_3PO_4$).

It realized if temperature is increased the amount of acid/alkali and reaction time can be decreased and vice versa.

The obtained material is preferably neutralised using an alkali, if latter of the hydrolysis steps involves an acid, and with an acid if the latter hydrolysis step involves an alkali. The acid and alkali are preferably suitable for human or animal use, preferably food grade.

In a preferred embodiment the invention is directed to method wherein at least the acid and alkaline hydrolysis and optionally the neutralization steps are performed in one container or reaction vessel. It is realized that this is beneficial increasing the effectiveness and reducing the costs of the process.

The material obtained, preferably neutralised, containing both insoluble and soluble fractions, from the hydrolysis step is further diluted in lower dry matter content/concentration what was used in the hydrolysis step and the material is contacted with an aqueous solution for a suitable time, preferably from about 30 min to about 2 hours, more preferably from about 45 min to 1 h 15 min and most preferably for about 1 hour. The contacting of hydrolysed, and preferably neutralised, material with an aqueous solution is to enhance solubilisation of soluble components of the material (see FIGS. 1 and 2).

In an alternative embodiment, the yeast cell material is separated into insoluble and soluble components before hydrolysis step, hydrolysis with an alkali and an acid is carried out for separated yeast cell material components and the soluble fractions are separated from the hydrolysed yeast cell material and soluble fractions are combined. Before combining soluble components both components can be contacted with an aqueous solution to enhance solubilisation of soluble fractions. Alternative embodiments of the invention and shown in FIG. 2.

In an alternative embodiment, the yeast cell material is first treated with an alkali, optionally neutralized, insoluble and soluble components are separated and the acid hydrolysis step is carried out for separated components. It is realized that the insoluble material is preferably hydrolysed under condition with higher acid amount and/or higher reaction temperature and/or longer reaction time. After acid hydrolysis soluble components are combined. Before combining soluble components both components can be contacted with an aqueous solution to enhance solubilisation of soluble fractions.

In an alternative embodiment, the yeast cell material is first treated with an acid, optionally neutralized, insoluble and soluble components are separated and the alkali hydrolysis step is carried out for separated components. It is realized that the insoluble material is preferably hydrolysed under condition with higher base amount and/or higher reaction temperature and/or longer reaction time. After alkali hydrolysis soluble components are combined. Before combining soluble components both components can be contacted with an aqueous solution to enhance solubilisation of soluble fractions.

In another embodiment, yeast cell material can be separated into soluble and insoluble components which can be processed with hydrolysis steps according to invention and thus obtained materials may be combined e.g. before and after neutralization step, contacted with an aqueous solution, mixed and fractionated to soluble and insoluble fractions. Thus obtained soluble fraction embodies a soluble immunostimulatory composition that contains saccharide fraction according to invention.

Figure 2:
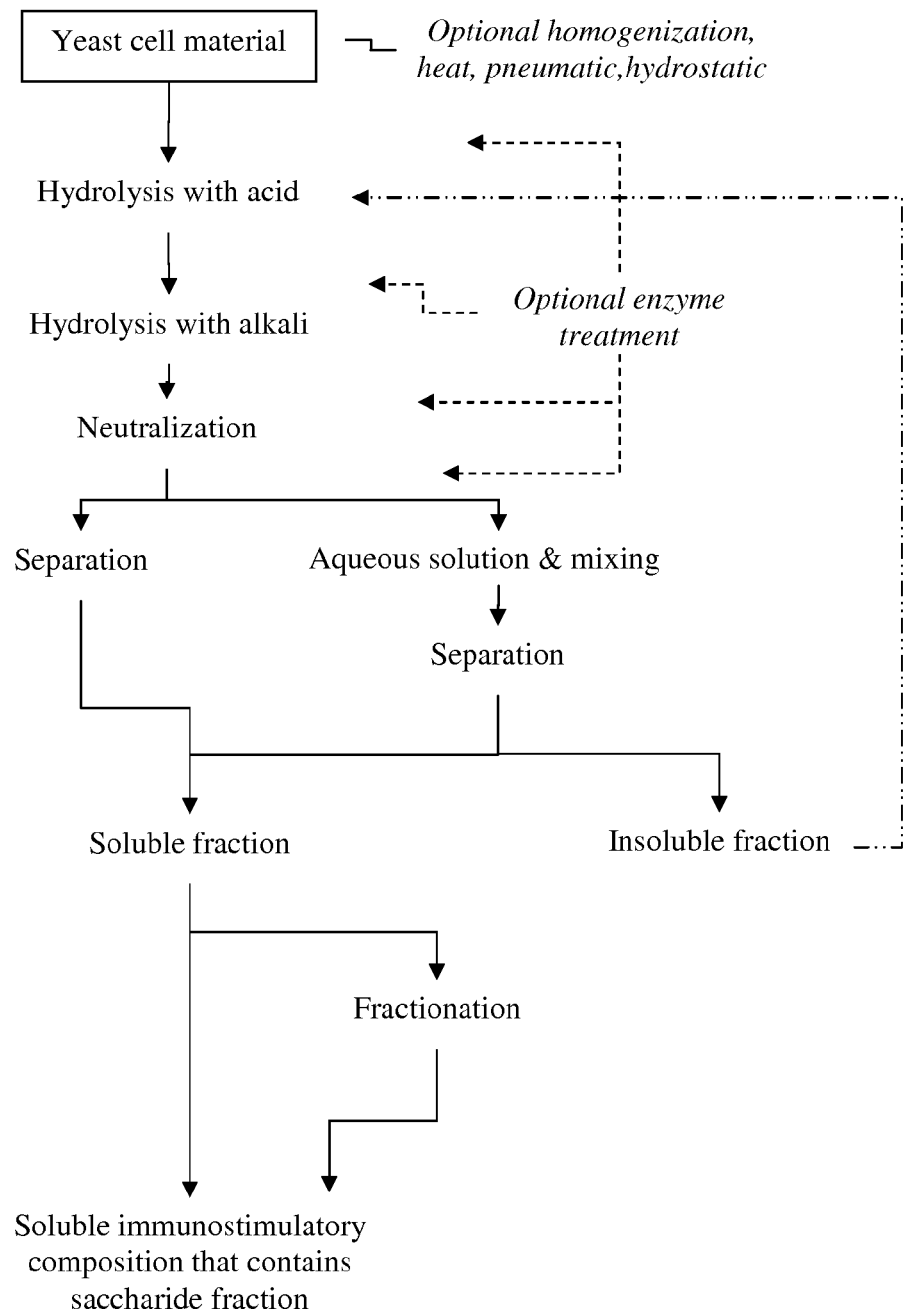
FIG. 2. A flowchart of another embodiment for process for production of soluble immunostimulatory composition that contains saccharide fraction in accordance with the present invention.
Figure 2:
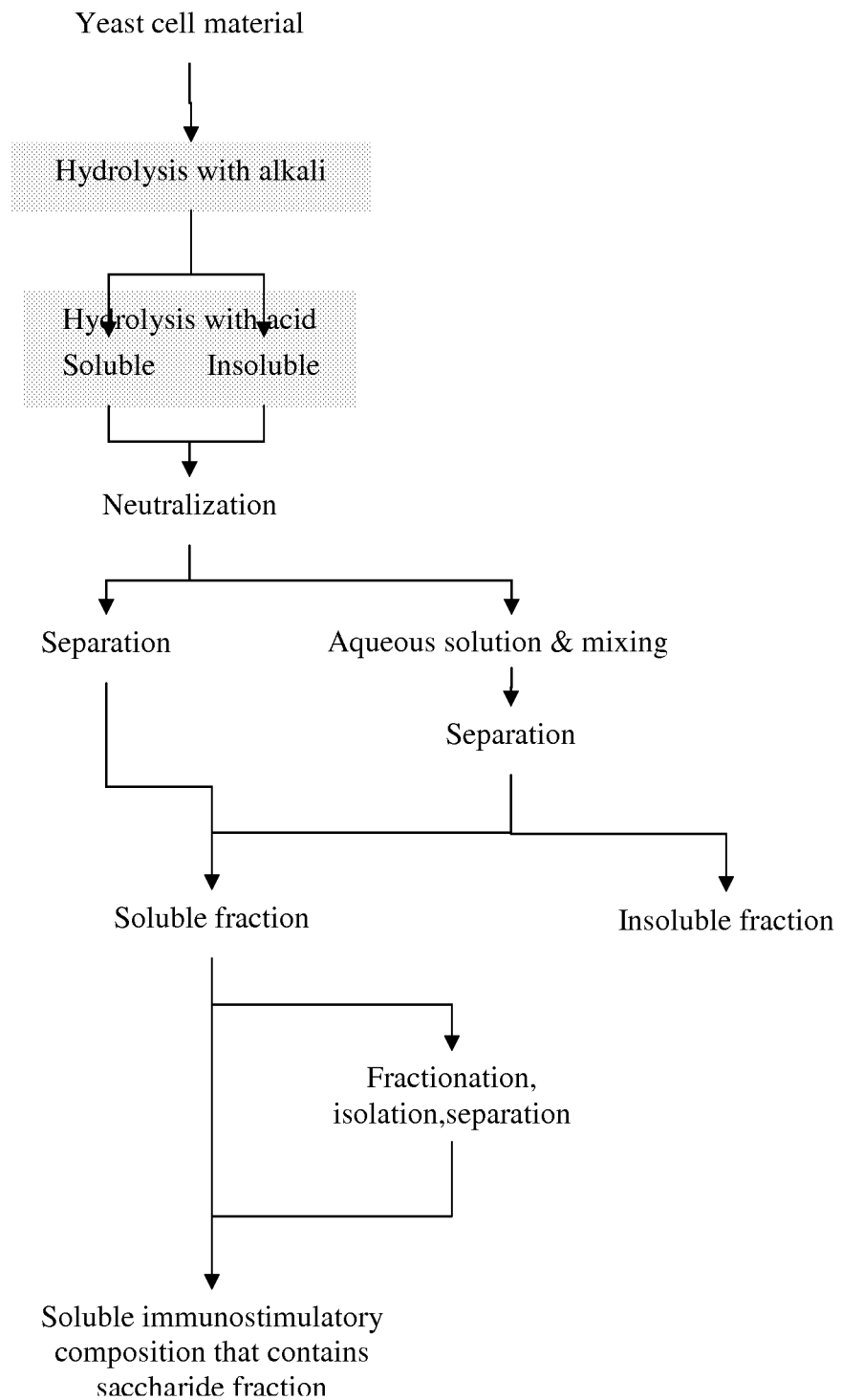
Figure 2:
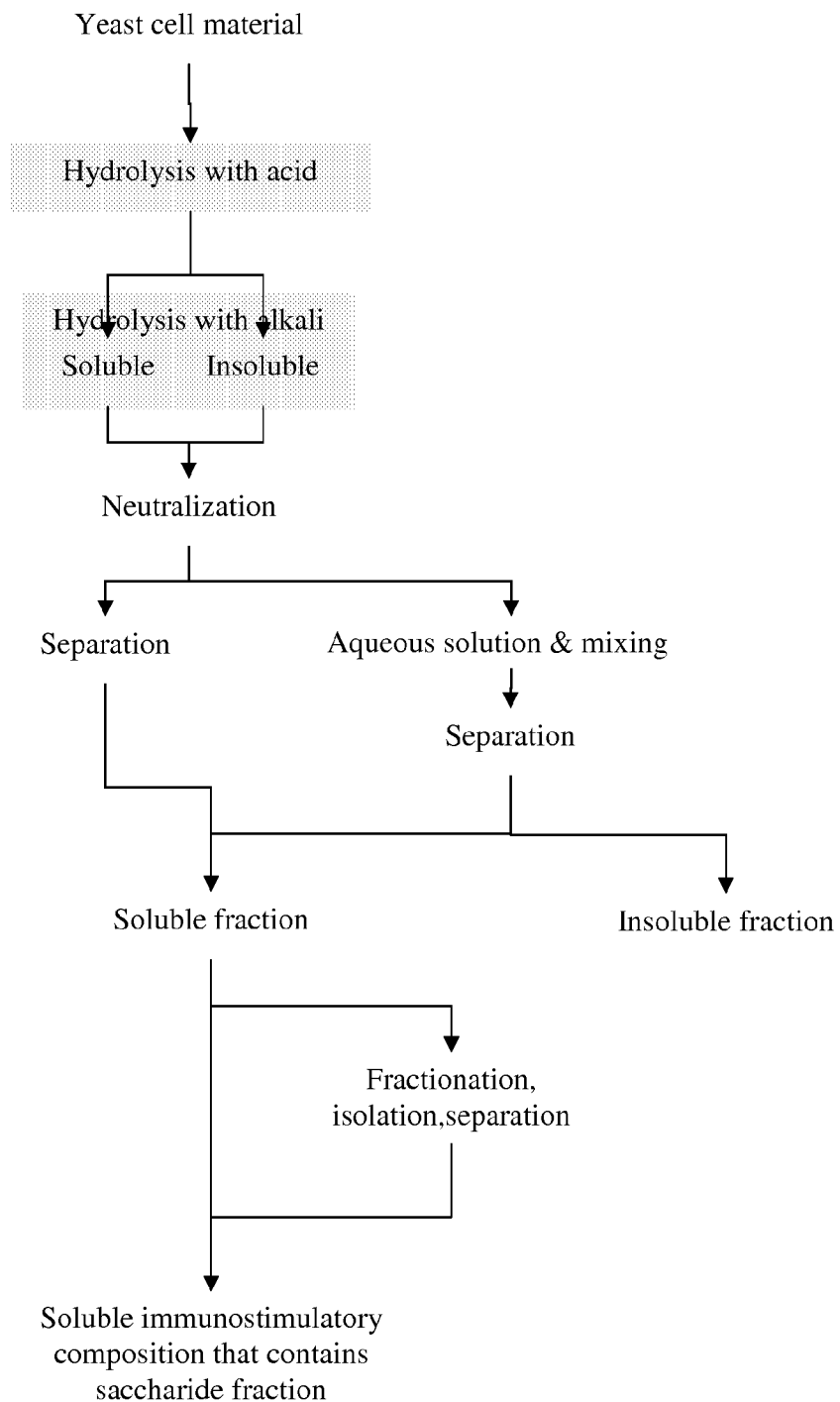

The material obtained, preferably neutralised, and optionally diluted into a lower dry matter content/concentration what was used in the hydrolysis step, is separated into soluble and insoluble fraction, preferably by centrifugation or filtration and discarding or recycling to the hydrolysis step the (aqueous) solution insoluble material (see FIGS. 1 and 2).

The obtained soluble fraction may be subjected to a fractionation step, by a chromatographic method and/or a phase separation solution method and/or ultrafiltration with a certain size exclusion criteria. Chromatographic methods include but are not limited to absorption of charged and or lipophilic (hydrophobic) impurities, size exclusion chromatography, or affinity chromatography.

Ultrafiltration may be performed with size exclusion or cut-off with 1000 Da, 2000 Da, or with 3000 Da or higher molecular weight cut-off. The preferred cut-off about 1000 Da, more preferred cut-off is about 3000 Da and most preferred cut-off is about 2000 Da. The salt, degradation impurities, and other small molecules, such as saccharide monomers, are filtered and immunostimulating saccharide components are retained in the fractionated and concentrated soluble fraction.

The preferred fractionation methods include industrial methods with suitable capacity and which can fractionate the preferred molecules, preferably gel filtration, ultrafiltration or precipitation, even more preferably precipitation or ultrafiltration.

Preferred precipitation methods include precipitation with solvent, preferably in low temperature from acid and alkali hydrolysis product optionally containing substantial amount of salts from hydrolysis steps or from desalted product.

The preferred fractionation is performed to separate less active molecules, a low molecular weight fraction from the product, preferably the low molecular weight molecules are smaller than about 500-5000 Da. In preferred embodiment the low molecular weight molecules to be separated have molecular weight lower than 500 Da, even more preferably have molecular weight lower than about 1000 Da, even more preferably have molecular weight lower than about 2000 Da, even more preferably have molecular weight lower than about 3000. The invention revealed that major part of active saccharide molecules are substantially larger that 5000 Da compared to Mw defined by glucose polymer standard. It is therefore in specific embodiment preferred to increase the speed of fractionation step, eg. filtration and remove low molecular weight material by method removing even larger molecules, preferably have molecular weight lower than about 4000 Da, even more removing molecules with molecular weight under 5 000 Da. It is realized the cut-off levels 2000 and 3000 removes oligosaccharide, which are less useful as monovalent molecules and peptides, which are not desired for the characteristics texture of the product and removal of low Mw fraction below 2000 or in a preferred embodiment.

The invention is especially directed to novel fractionated products produced by the size fractionation processes having essentially molecules with molecular weight above the removed low molecular weight fractions, preferably at least above 500 Da, even more preferably above 1000 Da, even more preferably above 2000 Da or most preferably above 3000 Da, and in specific embodiment of high production efficacy processes removing fraction Mw below 5000 Da or more preferably 4000 Da.

The ultrafiltration step may be carried out by forcing an extract produced from the processes described herein, such as a soluble fraction, through an ultrafilter under pressure. Suitably, the ultrafilter comprises one or more semi-permeable membranes. The semi-permeable membrane or ultrafilter may have a molecular weight cut-off of, for example, at least 1000 Da, particularly at least 1500 Da, and even more particularly at least 2000 Da. In some embodiments it may be preferred to use at least 3000 Da for high efficacy methods even cut-off 4000 or more, even more preferably cut-off 5000 Da or more. It is to be understood that the ultrafilter may have a molecular weight cut-off any value between those recited herein including, but not limited to, a molecular weight cut-off of at 500 Da, 1000 Da, 1500 Da, 2000 Da, 2500 Da, and 3000 Da, and under specific embodiment 3500 Da, 4000 Da, 4500 Da, and 5000 Da. Suitable ultrafilter membranes include, but are not limited to, hollow fiber membranes available from A/G Technology Corp, Needham, Mass. or cellulose membrane filters by Millipore. It is realized that skilled person can test and optimize suitable cut-off for separating the desired low molecular weight fraction for the ultrafiltration using available filtration membranes and suitable molecular weight standards preferably including carbohydrate molecular weight standard with hexose monosaccharide residues.

In a preferred embodiment the molecular filters cut-off is a practical value similar to cellululose membrane cut-off, more preferably Millipore cellulose membrane of Mw 1000 Da or Millipore cellulose membrane 3000 Da, or in other preferred embodiment cut-off corresponding to cut-off similar corresponding membranes with nominal cut-off (based on cut-off of membranes with Mw 1000 and 3000) between 500-2500 Da, more preferably 500-2000 Da, more preferably 1000-2000 Da and higher range (closer to cut-off 3000) 2000-5000 Da, more preferably between 2000-4000, or more preferably between 2500 and 3500 Da. It is realized that the ultrafiltration membranes may retent minor part of the lower Mw molecules and let through high Mw molecules.

The ultrafiltration step may optionally include passing the soluble fraction through two or more ultrafilters of different molecular weight cut-offs. The final fraction comprises an enriched saccharide composition wherein a majority of saccharides have a molecular weight falling between the molecular weight cut-offs of the ultrafilters, for such fraction the lower limit is the size of the lower Mw fraction to be removed according to the invention.

The soluble fraction can be further subjected to a fractionation step to purify, isolate, or separate the saccharide fraction. The purification, isolation or separation may be performed in the similar manner as described above or in the Examples.

The soluble immunostimulatory composition that contains saccharide fraction obtained according to the invention is substantially odourless and tasteless. These characteristics are useful when the soluble immunostimulatory composition that contains saccharide fraction is used in preparing food supplements, pharmaceuticals, and nutraceuticals. The odourless and tasteless (immunostimulatory) saccharide fraction obtained according to the invention may be used in preparing food supplements, additives, pharmaceuticals, and nutraceuticals.

The saccharide fraction of the soluble immunostimulatory composition according to present invention comprises typically mannans, beta 1,6 glucans and less than 8%, 7%, 6%, 5%, 4%, 3%, 2%, 1% or 0.1% or 0.05% of beta-1,3 glucan of dry matter. In a more preferred embodiment the saccharide fraction is essentially devoid of beta-1,3 glucan.

This exemplified process described above is shown in the flowchart of FIG. 1 and an alternative process in FIG. 2.

In a preferred embodiment production of a soluble immunostimulatory composition that contains saccharide fraction, the method comprises the steps of providing yeast cell material, preferably a brewer's yeast cell material, and subjecting yeast cell material to a hydrolysis with an alkali at a pH about 12 to 13 and a temperature of about 20° to 60° C. or about 60° to 90° C. for about 0.5 to 5 hours and an acid at a pH about 2 to 3 a temperature of about 70° to 90° C. for about 3 to 5 hour, followed by neutralising the obtained material, contacting the material with an aqueous solution so that solubilisation of soluble components is enhanced, preferably in the lower concentration or dry matter content in what the yeast cell material was used in hydrolysis steps, separating soluble and insoluble fractions from the material obtained, and subjecting the soluble fraction of previous step to fractionation with ultrafiltration, preferably using cut-off about 1000 to 2000 or 3000 Da, and reducing the ultrafiltrated fraction to a solid material.

The preparations and compositions and fractions of the invention may be dried by any suitable process including, but not limited to, freeze-drying, roller drum drying, oven-drying, spray-drying, ring-drying, and combinations thereof and/or dried using film-forming equipment, and either may be used without further processing, or may be milled using any suitable technique.

In an embodiment yeast cell material can be disrupted or any material in the steps of the method may be treated with heat and/or mechanically, pneumatically, and/or hydrostatically so that solubility of saccharide fraction is increased and/or to release mannans and glucans from yeast cell material and/or to release mannans and glucans from a material obtained in any step of the method. The yeast cell material, for example, brewer's yeast or brewer's cell cream can be homogenized before the step i) of the method of the present invention. In an alternative embodiment, physical homogenization and/or heat treatment or pneumatic, mechanic and/or hydrostatic treatment can be performed for any material obtained in the method of the invention.

Preferred purification, isolation or fractionation methods include removal of part of major non-saccharide components such as 1) desalting, in preferred embodiment by precipitation of salt such as precipitation of phosphate by calcium or other ions or using ultrafiltration, 2) removal of ionic molecules or hydrophobic molecules by specific adsorbents such as hydrophophic or ion exchange matrixes and/or 3) removal of the non-soluble material.

Purification or fractionation increases saccharide content of the saccharide fraction. Desalting by ultrafiltration after strong phosphoric acid hydrolysis increases the amount of saccharides in preparation. Preferably, soluble fraction obtained, preferably by ultrafiltration, and containing saccharide fraction is substantially tasteless and odourless and well suited for food additives and supplements and beverages and pharmaceutical compositions.

Fractionation, Purification or Isolation of Soluble Saccharide Fractions

The present invention is also directed to purified or enriched saccharide fractions comprising one or several of the saccharides, with increased biologic and immunostimulatory activity.

The preferred purification methods include following and combinations thereof a) chromatographic methods such as
   i. chromatographies for absorption of charged and or lipopholic (hydrophobic) impurities
   ii. size exclusion chromatography, especially gel filtration to remove low molecular weight impurities
   iii. affinity chromatographies with matrices binding to the saccharides or part thereof, preferably chromatography on activated carbon and/or b) phase separation solution methods such as extraction with solvents and/or precipitation of impurities or saccharides. In a preferred embodiment organic solvent is used for precipitation, preferably an alcohol or ketone such as methanol or ethanol, more preferably ethanol; or acetone is used for precipitation of the saccharides of preferred size.

and/or c) centrifugation and separation of solution and precipitant and/or d) chemical or enzymatic methods to degrade undesired components, preferably mild alkaline hydrolysis to degrade alkaline labile impurities and/or enzymatic hydrolysis of Glcα-comprising glycogen/starch type saccharides Solvents, for example those mentioned above, can be used to precipitate and/or wash materials of any step of the present method. In an embodiment an alkali hydrolysis step is carried out in the presence of a solvent, preferably an alcohol, such as ethanol.

In an embodiment enzymes may be used to degrade cellular components and/or enhance extraction of saccharide during the method of production of the soluble immunostimulatory composition that contains saccharide fraction of the invention.

The enzymatic step may utilize a high pH protease at an alkaline pH, for example, at a pH of at least 8.5, particularly at least 9, and more particularly at least 9.2. The pH may also suitably be less than 10.5, particularly less than 10, and even more particularly less than 9.5. The protease treatment may suitably be carried out at a temperature of at least 45° C. and particularly at least 50° C. The protease treatment may suitably be carried out at a temperature of less than 70° C., particularly less than 65° C., and more particularly less than 60° C. The protease treatment may be suitably carried out for at least 5 hours, particularly at least 8 hours, more particularly at least 10 hours, even more particularly at least 12 hours. The protease treatment may be suitably carried out for less than 48 hours, particularly less than 36 hours, more particularly less than 24 hours, and even more particularly less than 18 hours. The protease enzymatic step is preceded or followed by incubation with glucoamylase (e.g. from *Aspergillus* species), an amylase (e.g., α-amylases from *Bacillus subtili, Aspergillus oryzae*; amyloglucosidases from *Aspergillus niger* or *Rhizopus* mold) and/or a lipase (e.g., lipase from *Pseudomonas cepacia, Candida rugosa* and *Mucor javanicus*; typically about 0.05%-1% by weight). The incubation with glucoamylase, amylase and/or lipase is suitably carried out at neutral to slightly acidic pH and elevated temperature. For example, the pH may suitably range from at least 3.5, particularly from at least 4, and even more particularly from at least 4.5. The pH may also suitably range from less than 7, particularly less than 6, and even more particularly less than 5.5. The temperature for carrying out the incubation with glucoamylase, amylase and/or lipase may suitably range from at least 40° C., particularly at least 45° C., and more particularly at least 50° C. The temperature may also suitably range from less than 70° C., particularly less than 65° C., more particularly less than 60° C. Temperatures of at least 60° C., at least 65° C., at least 70° C., at least 75° C., at least 80° C., at least 85° C., or at least 90° C. may be suitably be used, particularly if the protease, amylase or lipase is a thermostable enzyme. The incubation with the alkaline protease can also be followed or preceded by incubation with a combination of a glucoamylase and a lipase, a combination of an amylase and a lipase or a combination of a glucoamylase, an amylase and a lipase.

Suitably, the high-pH protease may have an optimum proteolytic activity at a pH above 7. Suitable proteases include, but are not limited to, those obtained from *Actinidia chinensis, Ananas comosus, Aspergillus* spp. (e.g. *A. niger, A. niger* var. *awamori, A. oryzae, A. sojae, A. melleus*), *Bacillus* spp. (e.g. *B. subtilis, B. alcalophilus, B. amyloliquefaciens, B. halodurans, B. lentus, B. licheniformis, B. stearothermophilus, B. thermoproteolyticus*), *Carica papya, Cryphonectria parasitica, Endothia parasitica, Ficus glabrata, Kluyveromyces lactis, Penicillum citrinum, Rhizomucor miehei, Rhizopus niveus*, from calf, goat or ox stomachs or porcine pancreases, and combinations thereof. Suitable proteases may include, but are not limited to, commercially available enzymes such as subtilisin Carlsberg, subtilisin BPN', subtilisin Novo, subtilisin 309, subtilisin 147 and subtilisin 168, Alcalase™, Savinase™, Primase™, Duralase™ Durazym™, Esperase™, and Kannase™. (available from Novo Nordisk A/S); Maxatase™ Maxacal™, Maxapem™, Optimase™, Properase™, Purafect™, Purafect OxP™, FN2™, and FN3™ (available from Genencor International Inc.); and Validase™ AFP, Validase™ FP Concentrate, Validase™ FP 500, Validase™ FP II, Validase™ TSP Concentrate, Alkaline Protease Concentrate, Bromelain (available from Valley Research, South Bend, Ind.), and combinations thereof.

Suitable amylases include those of plant, animal, bacterial or fungal origin, and combinations thereof. Amylases include, but are not limited to, glucoamylases or α-amylases obtained from *Bacillus* spp., (e.g., *B. licheniformis, B. amyloliquefaciens, B. subtilis, B. stearothermophilus*), *Aspergillus oryzae, Aspergillus niger, Aspergillus niger* var. *awamori, Microbacterium imperiale, Thermomonospora viridis*, barley malt (*Hordeum* spp.), porcine pancreas (*Sus* spp.), and combinations thereof. Examples of useful amylases include, but are not limited to, commercially available amylases such as Glucoamylase Concentrate, Duramyl™, Termamyl™, Fungamyl™ and BAN™ (available from Novo Nordisk A/S); Rapidase™ and Purastar™ (available from Genencor International Inc.); and Validase™ BAA, Validasem™ HT340L, Validase™ FAA, Validase™ AGS, Validase™ GA, Validase™ RGA (available from Valley Research, South Bend, Ind.), and combinations thereof. The amylase may be suitably used at a final concentration of at least 0.001%, particularly at least 0.01% and even more particularly at least 0.02%. The amylase may be suitably used at a final concentration of less than 0.1%, particularly less than 0.05%, and even more particularly less than 0.1%.

Lipases useful in the invention include, but are not limited to, lipases from *Humicola* (synonym *Thermomyces*), e.g. from *H. lanuginosa* (*T. lanuginosus*), *H. insolens*, a *Pseudomonas* lipase, e.g. from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g. from *B. subtilis, B. stearothermophilus* or *B. pumilus* (WO 91/16422); *Aspergillus oryzae, Aspergillus niger, Candida lipolytica, Candida rugosa, Mucor javanicus, Penicillum roqueforti, Rhizomucor miehei, Rhizopus delemar, Rhizopus niveus*, Rhizopusoryzae, *Rhizopus arrhizus*, and combinations thereof. Commercially available lipase enzymes include, but are not limited to, Lipolase™ and Lipolase Ultra™ (Novo Nordisk A/S), and Fungal Lipase 8000 and Pancreatic Lipase 250 (available from Valley Research, South Bend, Ind.).

Novel Compositions

The structures of the compositions were studied by NMR as shown in EXAMPLE 2 and by chromatography in EXAMPLE 3.

The invention is directed to novel soluble immunostimulatory composition that contains saccharide fraction and wherein saccharide fraction comprises mannans and beta-1,6 glucans and less than 1% of beta-1,3 glucan of dry matter, and preferably the amount of β3-glucans is less than 50% of the β6-glucans, and wherein the composition is substantially odourless and tasteless.

The preferred saccharide compositions are soluble, preferably at least 95% soluble even more preferably 98% soluble, even more preferably 99% soluble and most preferable 100% soluble in water at least as 1% w/w solution, in a preferred embodiments also as 1.5% or 2.0% solution. In a preferred embodiment the total solubility of the composition is between 98% and 100%, preferably 100% as 1% w/w solution in water.

The inventors used NMR spectrometry to reveal amounts of specific soluble mannan and b6-glucan components according to the invention. The NMR was calibrated with an in internal standard and the amount of monosaccharide epitopes were analyzed from integrals of the NMR spectrum revealing following components, as shown in EXAMPLE 2 and FIG. 3

The preferred composition comprises rare soluble β1-6 glucan 0.001-10%, more preferably 0.005-5%, even more preferably 0.01-3%, and even most preferably 0.01-1.5% w/w, and in a preferred embodiment about 0.32% w/w of the dry weight.

The preferred composition comprises novel soluble mannan 1-50%, more preferably 2-50%, even more preferably 3-50%, even more preferably 4-50%, even more preferably 4-40%, even more preferably 5-35%, most preferably 5-25% or 10-20% w/w of the dry weight and in a preferred embodiment about 14% w/w.

The data revealed that the method increased the substantially the amount of soluble mannan but not the β6-glycan in the composition compared to an optimized acid hydrolysis method to increase the amount of soluble molecules. In a preferred embodiment the novel composition comprises soluble mannan and β6-glucan in ratio of 4.4 μmol to 0.016 μmol (14% to 0.32%). This is very different ration from compared to methods using only acid hydrolysis and producing much less mannose glycans.

The saccharide fraction resulting from the methods of the invention comprise mannans:glucans in ratio as 14:0.32 or higher than 40:1 or β6-glucan or β-glucans or, preferably less than 20% w/w, more preferably less than 10% w/w, more preferably less than 5% w/w, more preferably less than 4%, even more preferably less than 3.5%, even more preferably less than 2.5%, most preferably less than 2.3% of the mannans on dry weight basis.

The amount of the soluble β-glucan and mannan was in a preferred embodiment at least about 14% w/w, more preferably at least about 15% w/w of the dry weight of the composition, and it can be substantially increased by optimization and/or removal of starch, preferably at least to 19% w/w.

The product resulting from the methods of the invention comprise at least about 10%, particularly at least about 14%, more particularly at least about 15% saccharides, even more particularly at least about 16% saccharides of the total product on a dry solids basis (w/w), wherein the saccharides are soluble β-glucan and α-mannose oligo/polysaccharide materials, preferably essentially polysaccharides. The composition comprises optionally soluble starch residue from about 5 to 50%, preferably 10-25%. In a preferred embodiment the starch is removed e.g. by amylase treatment and the amount of soluble β-glucan and α-mannose oligo/polysaccharide materials is increased accordingly.

The saccharide fraction resulting from the methods of the invention comprise at least 75%, particularly at least 80% and more particularly at least 85% mannans of the total cell wall β6-glucan and α-mannan saccharides on a dry solids basis.

In a specific embodiment the saccharide fraction resulting from the methods of the invention comprise at least 1%, particularly at least 2%, more particularly at least 2.2% and more particularly at least 2.3% of beta 1-6 glucans of the total saccharides on a dry solids basis.

The product also suitably comprises less than 8%, particularly less than 2%, more particularly less than 1%, more particularly less than 0.5%, more particularly less than 0.1%, even more particularly less than 0.06% β1-3-glucans of the total cell wall β6-glucan and α-mannan saccharides on a dry solids basis.

The product also suitably comprises less than 8%, particularly less than 2%, more particularly less than 1%, more particularly less than 0.5%, more particularly less than 0.1%, even more particularly less than 0.05%, even more particularly less than 0.01% of β1-3-glucans of the total composition mass on a dry solids basis.

Figure 3:
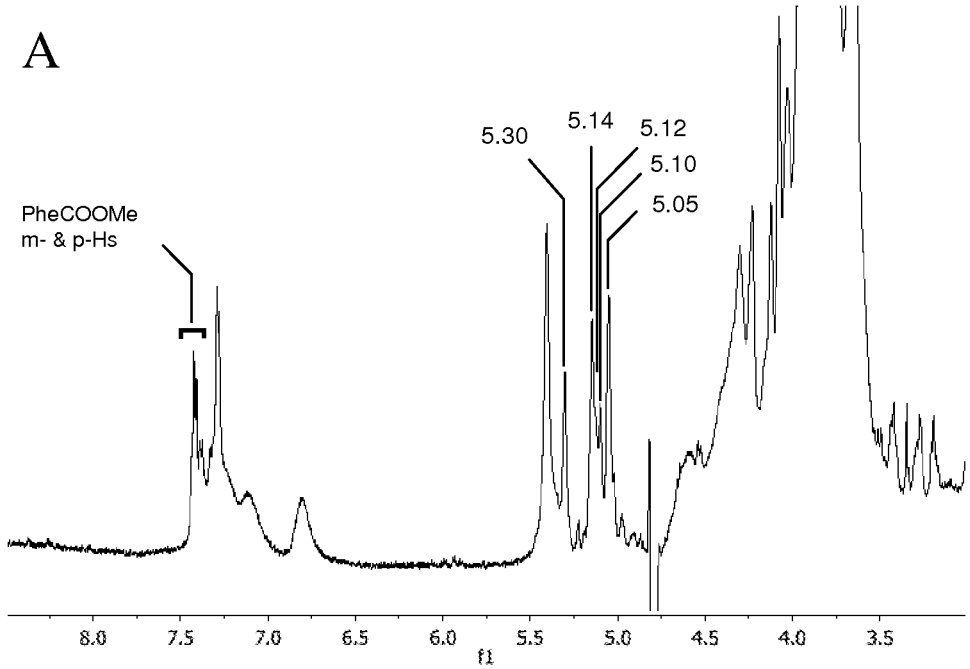
FIG. 3. Quantitation of soluble carbohydrate components by NMR. The material prepared as shown in Example 1 (A) and a sample of commercial acid hydrolyzed yeast material (B) were dissolved in deuterium oxide. 0.5 μmol of phenylalanine methyl ester (PheCOOMe) was added for quantitation standard. PheCOOMe protons and yeast mannan signals quantitated by integration are indicated.
Figure 3:
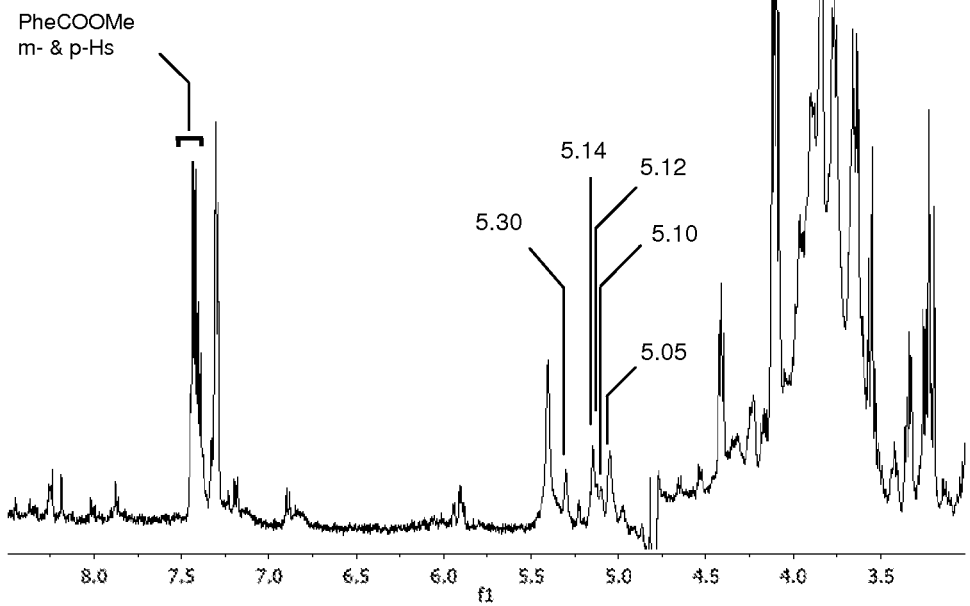

The NMR data further revealed the major structural features of the soluble a-mannan, as shown in FIG. 3 and Example 2, The composition comprises terminal Manα3 (Manα2)$_m$Manα6-, and Manα2Manα6- and Manα2 (Manα2)$_n$Manα6 structures, wherein m and n are integers from 1 to 10, independently and the Manα6-structures can form a polyvalent carrier comprising a polymer of the Manα6-residues, and preferably there is about equimolar amount of Manα2- and Manα3-non reducing end terminal structures, preferably similarly as observable from a NMR spectrum.

Size Distributions of the Novel Soluble Mannans and Glucan

At least 80% (w/w), particularly at least 85% (w/w), more particularly at least 90% (w/w), even more particularly at least 91% (w/w) of the total mannans in the saccharide fraction may have a molecular weight above 3000 Da.

In a preferred embodiment the mannans and glucans have a molecular weight of at least 500 Da, more preferably at least 1000 Da.

Figure 4:
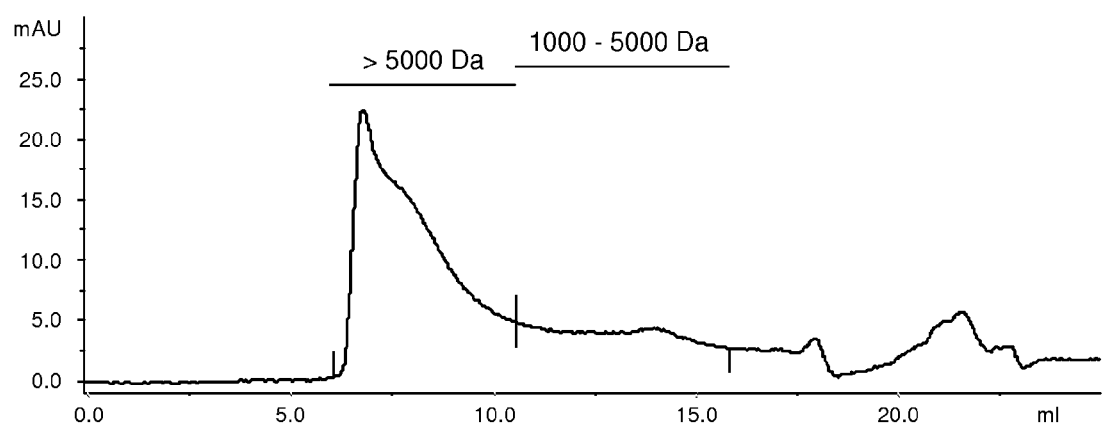
FIG. 4. Superdex Peptide chromatogram of 2-AB derivatized saccharide fraction analyzed at 336 nm. 2-AB derivatized dextran 5000 and dextran 1000 standards elute in this system at 10.5 min and 15.8 min, respectively. The relative abundance of the material with MW>5000 Da and between 1000-5000 Da were calculated from the chromatogram area as indicated in the figure.

The inventors further studied the preferred compositions by gel filtration chromatography as shown in FIG. 4, see also Example 3, and the preferred composition comprises major part of glucan and mannan saccharide materials eluting between void volume and position of hexose polysaccharide Mw marker of 5000 Da, and optionally a minor portion of the material eluting between Mw markers of 1000 and 5000 Da, when the Mw marker of 5000 elutes at about 10.5 min, and the Mw marker of about 15.8 min form Superdex Peptide 10/300 GL column with total elution volume of 18 ml and column length 30 cm and when the carbohydrates are analyzed as reducing end diaminobenzene (2-AB) labeled structures.

The data analyzed in EXAMPLE 3 reveled that the preferred composition comprises at least about 50%, more preferably at least about 70%, even more preferably at least about 73% more preferably at least about 80 mol %, and in preferred embodiment at least about 85%, more preferably at least about 87% of materials larger than 5000 Da and about 13-20 mol % of materials eluting between Mw markers of 1000 and 5000 Da.

Based on the molar amount and molecular weight distribution it can be estimated that the present composition comprise very minor amounts of oligosaccharide materials, especially after gelfiltatrion with cut-off 1000 Da and even more preferably with cut-off 2000 Da or 3000 Da. On weight basis the composition comprises at least about 91% (w/w) of soluble saccharides preferably mannan materials, including all three α-mannan types according to the invention, larger than 5000 Da, more preferably at least 95% w/w, even more preferably at least 97% w/w, more preferably at least 98% w/w, and most preferably at least 95% w/w. It is realized that this is very different from acid hydrolysis products optimized for soluble oligosaccharide composition of a previous PCT patent application of the inventors comprising preferably at least more than 10% of specific mannan oligosaccharides.

Specifically the preferred higher molecular weight polysaccharide composition of present invention comprises less than 10% more preferably less than 5%, more preferably less than 2% w/w of Manα3Manα2-mannose oligosaccharides or other mannose saccharides eluting between 12-16 min as non-derivatized sacchariddes when calculated as portion of total Manα3Manα2-mannose comprising saccharides.

The invention revealed that it is possible to produce soluble polysaccharide with relatively molecular weight as shown by the gel filtration experiment. The preferred composition comprises major part of saccharide materials eluting at void volume of the Superdex column and another major portion eluting as a high shoulder of the peak at the void volume at about 7 min, preferably as shown in FIG. 4. The invention is directed to the soluble polysaccharide materials having similar absorbance pattern and absorptivities as 2AB labelled conjugates, as shown in FIG. 4, under the gel filtration and labeling experimental conditions of Example 3.

Specific Embodiments

The invention is directed to novel compositions according to the invention the molecular weight of the structures is above 4000 Da or 5000 Da and material is water soluble.

The invention is directed to novel composition is in essentially dry form. It is realized that the compositions are especially useful in dry form. The Dry form contain preferably less than 30%, more preferably less than 20%, even more preferably less than 10% and most preferably less than 5% of water, preferably at least when the composition is produce or packed.

The invention is directed to a food supplement, pharmaceutical, or nutraceutical comprising the composition of comprising the composition according to the invention.

The invention is directed to therapeutic composition comprising a composition according to the invention selected from a group: a medicine, clinical nutrition composition haven pharmaceutical activity, nutraceutical therapeutic composition with pharmaceutical activity for use as a medicine.

The invention is directed to a therapeutic composition according to the invention wherein the composition is for use of prophylaxis or treatment of a disease wherein immunomodulatory activity is needed and/or for antiadhesion therapy against pathogens.

The invention is directed to use of composition of any of the claims for production of a medicine for a treatment of condition needing immunomodulatory therapy or antiadhesion therapy.

The invention is directed to methods of treatment involving a step of administering a therapeutic composition of invention to a patient.

The preparations and compositions in accordance with the present invention are contemplated to be of value in, e.g., food supplements, pharmaceuticals (e.g., improving immune response), animal feeds, and nutraceuticals. For example, a therapeutic composition or medicine, a food or an animal feed may suitably contain 0.050 g to 50 g, more preferably 0.1 g to 30 g of preparation/kg food or feed. Suitably, the preparation may be comprise at least 0.005%, particularly at least 0.01%, more particularly at least 0.02%, more particularly at least 0.05%, and even more particularly at least 0.1% and less than 5%, particularly less than 2%, more particularly less than 0.5%, and even more particularly less than 0.3% of the total weight of the food or feed, on a weight/weight basis. Suitable animal feeds include, but are not limited to, cattle, horse, swine, poultry, fish (e.g., crustacean, shellfish), bird and pet (e.g., cat, dog) feeds. A liquid composition may contain 0.1%-4% by weight of the preparation in accordance with the present invention. There are also numerous uses for the soluble immunostimulatory compositions that contains saccharide fraction or saccharide fraction alone made according to the present invention. For example, soluble immunostimulatory compositions that contains saccharide fraction or saccharide fraction alone may be used in the animal feed industry, having advantageously the ability to bind mycotoxins and also pathogenic bacteria, preventing bacteria from colonizing the intestinal tract.

In a preferred embodiment the invention is directed to highly effective therapeutic/medicine/food/feed compositions comprising less than 2% (weight/weight) of the composition according to the invention, even more preferably less than 1%, and most preferably less than 0.5%, in a preferred embodiment the active concentration being between 0.0001%-2%, more preferably between 0.001%-1%, even more preferably between 0.001%-0.5%, even more preferably between 0.001%-0.1%, even more preferably between 0.001%-0.05%, even more preferably between 0.001%-0.04%, even more preferably between 0.001%-0.025%, and even more preferably between 0.001%-0.01%. These highly effective concentrations are especially preferred for immunomodulation. In a preferred embodiment the compositions for antiadhesion are applied in the previous concentrations multiplied by 5 e.g between 0.0005%-10%, and 0.005-5%, and 0.005%-0.2% and 0.005%-0.05%, or multiplied by 10 e.g. 0.0010%-20%, and 0.010-10%, and 0.010%-0.4% and 0.01%-0.1%. In case the product is supplement the concentration is preferably counted as final formulation concentrations for the use by the human patient or animal. It is realized that the present composition with increasing amounts of effective compounds can be used in lower doses reducing costs and possible side effects of treatments.

For example, the (food) supplement comprising soluble immunostimulatory compositions that contains saccharide fraction or saccharide fractions alone made according to the present invention may suitably be used as immune stimulators in animal and human foods and beverages, pharmaceuticals or emollients, agents to reduce cholesterol. If added to an emollient, lotion or cream and used to treat a condition, the soluble immunostimulatory compositions that contains saccharide fraction or saccharide fractions alone may be suitably present at a concentration (w/w) of at least 0.05%, particularly at least 0.1% and more particularly at least 0.5%, and less than 10%, particularly less than 5% and more particularly less than 2%. Suitably, the soluble immunostimulatory compositions, which contain a saccharide fraction or saccharide fractions alone made according to the present invention may be used to treat eczema, for example, by incorporation into a cream, lotion or emollient. Eczema encompasses various inflamed skin conditions, including atopic dermatitis ("atopic eczema"), and affects about 10% to about 20% of the world population during childhood. Eczema appears to be an abnormal response of the body's immune system.

Thus, in an aspect of the invention, preferred embodiments include but are not limited to a compositions for nutrition or therapy, preferably including e.g. food composition, food supplement compositions, diet food compositions, pharmaceutical composition including prescription and OTC-drug compositions, clinical nutrition compositions, topical medicine compositions, natural medicine compositions, nutraceutical composition and nutraceutical additives. The compositions are aimed for the use by subject or patient in the need of the composition, preferably by human or animal, and most preferably by a human subject. It is considered that the concepts of medicine or pharmaceutical according to the invention includes prescription and OTC-drugs, therapeutic clinical nutrition compositions, topical medicine compositions, natural medicine compositions, nutraceutical composition with therapeutic effect and nutraceutical additives with therapeutic.

It is also possible to use the substance according to the invention in a food-stuff, or in a nutritional composition, both for humans and animals, for example in food, milk, yoghurt, or other dairy product, beverage compositions and infant formula foods. The nutritional composition or food-stuff described here is not natural human milk. It is preferred to use the substance according to invention as a part of a so called functional or functionalised food. The said functional food has a positive effect on the health of the person or the animal by an immunostimulatory effect or by inhibiting or preventing the binding of pathogens to target cells or tissues, especially in gastrointestinal tract. The substance according to the invention can be a part of defined food or functional food composition. The functional food can contain other known food ingredients accepted by authorities controlling food like Food and Drug Administration in USA. The substance according to invention can be also used as nutritional additive, preferentially as a food or a beverage additive to produce a functional food or a functional beverage. Foods and food compositions or supplements contain at least some regular major nutrients such as fats, proteins and carbohydrates, and preferably nutrients required in low amounts such as vitamins, minerals and salts.

The invention is further directed to use of the novel saccharide fractions in methods for production of pharmaceutical and/or therapeutic and/or nutraceutical compositions, preferably when the compositions are aimed for the use for subject or patient in the need of immunomodulation or immunostimulation or anti-infectious treatment.

The present food additive or (functional or food) supplement comprising soluble immunostimulatory composition that contains saccharide fraction or saccharide fraction alone manufactured or prepared by the method of the invention can be administered orally, or enterally. The form in which the food additive or supplement comprising soluble immunostimulatory composition that contains saccharide fraction will be administered (e.g., powder, tablet, capsule, suspension, solution, emulsion) will depend on the patient and the particular treatment. The quantity of the preparation, supplement or composition to be administered will be determined on an individual basis, and will be based in part on consideration of the condition of the subject, the subject's overall health, and the severity of the immunostimulatory disorder being treated or alleviated.

The supplement or additive comprising soluble immunostimulatory composition that contains saccharide fraction or saccharide fraction alone may be administered orally, in liquid or solid form, either at room temperature or chilled, or enterally through a feeding tube. The soluble immunostimulatory composition that contains saccharide fraction, or any supplement or additive comprising the same can be administered alone, in a biologically acceptable carrier (e.g., saline or water) with other ingredients such as vitamins and minerals, or as part of a complete-nutritional food. For example, soluble immunostimulatory composition that contains saccharide fraction or saccharide fraction alone can be administered as a component in a high fiber liquid food for oral or enteral feeding, by continuous or intermittent drip into a feeding tube (e.g., nasogastric, nasoduodenal, jejunal). The preparation comprising the soluble immunostimulatory composition that contains saccharide fraction or saccharide fraction alone of the present invention or any supplement or additive comprising the same can optionally include, other components, which will be determined primarily by the manner in which the composition is to be administered. For example, a preparation or compositions is to be administered orally in tablet or powder form can include, in addition to soluble immunostimulatory composition that contains saccharide fraction, a filler (e.g., corn starch, sucrose, lactose), a binder (e.g., carboxymethyl cellulose, gum arabic, gelatin), an adjuvant, a flavoring agent, a coloring agent, and/or a coating material (e.g., wax or plasticizer) and/or other nutritional supplements. A preparation comprising soluble immunostimulatory composition that contains saccharide fraction to be administered in liquid form can include composition manufactured by the method of the invention and, optionally, an emulsifying agent, a diluent (e.g., water, sterile saline) and/or a coloring or flavoring agent, or combined in a complete feeding formula to be administered orally or by feeding tube into the digestive tract. A complete feeding formula can contain all nutritional requirements. For example, such a feeding formula for oral or enteral administration could contain soluble immunostimulatory composition that contains saccharide fraction manufactured by the method of the invention, water, a source of carbohydrate (e.g., sucrose, hydrolyzed corn starch), an oil (e.g., corn or soybean oil), selected sources of vitamins (e.g., choline, chloride, ascorbic acid, alpha-tocophenyl acetate, niacinamide, calcium pantothenate, thiamine, riboflavin, phylloquinone, cyanocobalamin, vitamin $D_3$); selected sources of minerals (e.g., potassium citrate, magnesium chloride, calcium phosphate tribasic, sodium citrate, potassium chloride, zinc sulfate); a source of protein (e.g., soy protein isolate, calcium caseinate), and lecithin.

Further Purification

The invention is further directed to soluble saccharide fraction obtained according to the method of invention or a soluble saccharide fraction obtained by further purification step from the said fraction. The further purification may is preferably selected from the group of removing proteins, lipids, aromatic molecules, or ionic molecules by chromatographic methods, preferably hydrophobic or ion exchange or reverse phase methods or further size fractionation. The further purification is preferably aiming for isolation of mannan and/or b-glycan materials optionally with soluble starch component. In a specific embodiment the starch is degraded by amylase in preferred embodiments after at least one of the hydrolysis steps, preferably after acid hydrolysis and the resulting glucose and/or malto-oligosaccharides are removed by fractionation according to the invention or by separate fractionation.

The invention is further directed to the use of the saccharide fraction for use in immunostimulation in humans or animals, and for use in manufacturing a food or beverage or therapeutic or pharmaceutical or medicine for immunostimulation and/or antiadhesion in humans of animals.

The invention is further directed to the method according to the invention, further comprising using the soluble fraction of step iii) or iv) in a human or animal food or feed.

The invention is further directed to the method according to the invention, further comprising using the soluble fraction of step iii) or iv) in a product selected from a food supplement, pharmaceutical, cosmetic and nutraceutical.

The invention is further directed to the soluble yeast derived composition comprising saccharide fraction according to the invention or further purified saccharide composition for use in immunostimulation in humans or animals and/or for use in manufacturing a food or beverage for immunostimulation in humans of animals,
preferably wherein food is a solid food or a dairy product or food product comprising milk components or an infant formula
or wherein
the beverage is a therapeutic beverage or dairy beverage product or infant formula or a composition for producing a dairy beverage product or an infant formula by adding liquid.

High Yield Processes Using Acids and Bases
General Process
Alkaline Hydrolysis Above pH 9

The preferred process includes alkaline treatment combined with strong acid hydrolysis.

The preferred alkaline treatments include treatment alkaline solution with final reaction pH over 8, more preferably over 9, more preferably over 9.5, even more preferably over 10, even more preferably over 11, even more preferably over 11, even more preferably over 12, even more preferably 13 or even more preferably up to 13.5 over. The preferred range of alkaline conditions varies from pH 9 to 14, more preferably from 9.5 to 13.5. The time of the alkaline treatment is from 10 min to 24 h, more preferably from 0.5 h to 18 h, for short reactions even more preferably from 1 h to 12 h, in a preferred embodiment between 1 and 8 hours and in another preferred embodiment for quick reaction between 1 and 6 hours, even more preferably between 1.5 and 3.5 hours, most preferably about 2.25 hours with marginal +/−1 hour, +/−0.5 hour, +/−0.25 hour. Preferred long reactions are between 8-30 hours, more preferably between 8-24 hours, more preferably between 8-20 hours.

The preferred temperatures are for alkaline reactions are between 0-100 degrees of Celsius, more preferably between 10-90 degrees of Celsius. The preferred temperatures are for mild reactions are from 0-60 degrees of Celsius, preferably between 10-60 degrees, for a lowest range (in an embodiment including washing reactions) preferably between 10-45 degrees, preferably between 15-40 degrees, more preferably between 18-35 degrees, most preferably between 20-30 degrees of Celsius and for a higher range for optimized mild reactions to avoid degradation from between 35-60 degrees of Celsius, more preferably between 40-60 degrees, more preferably between 45-60 degrees of Celsius. Preferred higher ranges are between 60-100 degrees of Celsius, more preferably between 65-100 degrees of Celsius, more preferably between 70-100 degrees of Celsius, more preferably between 70-95 degrees of Celsius, and most preferably between 70-90 degrees of Celsius, or about 80 degrees of Celsius, with +/− marginal of 7, more preferably 5 and most preferably 4 degrees.

Optimization of the Alkaline Hydrolysis Sand Order of the Acid/Alkaline Hydrolysis The examples 12 and 13 show examples present highly effective high yield hydrolysis processes for the production and the effect of optimized alkaline hydrolysis Table 1 with high mannose content shown in Table 2.

General Process

The preferred process includes alkaline treatment combined with strong acid hydrolysis.

Mild Reactions with Strong Alkaline Including Washing

The alkaline treatments include the mild alkaline conditions with preferred low or close to room temperature ranges including and within 0 to 60 degrees of Celsius, more preferably between 10-45 degrees. The mild conditions include washing with a solvent not dissolving the polysaccharide, including preferably reasonably safe solutions and non-toxic solvent such as alcohol, preferably ethanol, containing solutions containing the alkaline e.g. between pH 9-14, more preferably between pH 9-13, more between pH 9-12.5, more between pH 9.5-12, more preferably more between pH 10-12 or about 11.0. The reaction times are very quick from 0.1 to 3 h or more preferably 0.5-2 h, or quick reaction between 1 and 6 hours and preferred ranges therein. Preferred alcohol is ethanol, the function of the solvent is to keep the polysaccharides in solid state while having some hydrolysis and washing effects. The concentration of the base such as alkaline hydroxide, such as NaOH is preferably between 1 mM or 1 M, preferably about 0.1 M with a range of +/−0.7 M (it is between 0.3-1.7 M), more preferably +/−0.5 M, more preferably +/−0.3 M. The concentration of ethanol is preferably between 65-95%, more preferably between 70-90%, more preferably between 73-87%, more preferably between 75-85%, or about 80%. The concentration of ethanol is adjusted to keep the alkaline in solution.

The Table 2 shows that washing with alkaline can surprisingly increase the purity of the acid hydrolysis mannan product from about 15 to about 20%. This would be considerably increase in the yield. In a specific embodiment the alkaline washing is performed after the acid hydrolysis.

Medium Strong Alkaline Hydrolysis Treatment

The invention revealed that medium strong alkaline reactions produce effectively highly pure glycan composition. E.g. example 14 and Table 2 show that the highest relative amount (purity) of mannans, 23.5% (w/w) of extracted product, is obtained in a process where yeast material is hydrolyzed first at pH 10 and then at pH 2.5, according to Example 12. High purity of mannans, 19.3% (w/w), is also obtained when the hydrolysis steps are reversed, as described in Example 13.

In separately preferred embodiment the invention is directed to the reaction where acid hydrolysis is first followed by alkaline hydrolysis and in the other embodiment preferably alkaline hydrolysis is performed first and then acid hydrolysis. The medium strong alkaline hydrolysis reactions are preferred because of the high yield of the pure mannans and because of limited side reactions such as colouring.

The medium strong alkaline hydrolysis is performed e.g. between pH 8.5-14, more preferably between pH 8.5-13, more between pH 9-12.5, more between pH 9-12, more preferably more between pH 9.0-11.5, even more preferably between pH 9.0-11 or about 10 with +/− marginal of 0.7, more preferably 0.5 and most preferably 0.3 pH units (e.g. pH between 9.7 and 10.3). Preferably the reaction temperatures for medium strong alkaline hydrolysis within the higher temperature ranges are between 60-100 degrees of Celsius, more preferably between 65-100 degrees of Celsius, more preferably between 70-100 degrees of Celsius, more preferably between 70-95 degrees of Celsius, and most preferably between 70-90 degrees of Celsius, or about 80 degrees of Celsius, with +/− marginal of 7, more preferably 5 and most preferably 4 degrees. The reaction times are 10 min to 24 h, more preferably from 0.5 h to 18 h, for short reactions even more preferably from 1 h to 12 h, in a preferred embodiment between 1 and 8 hours and in another preferred embodiment for quick reaction between 1 and 6 hours, even more preferably between 1.5 and 3.5 hours, most preferably about 2.25 hours with marginal +/−1 hour, +/−0.5 hour, +/−0.25 hour. In separate embodiment preferred long reactions are between 8-30 hours, more preferably between 8-24 hours, more preferably between 8-20 hours.

Strong Alkaline Hydrolysis Treatment

The invention revealed that strong alkaline reactions produce effectively highest amounts of preferred glycan composition. E.g. example 14 and Table 2 show that the highest total yield of the preferred mannans and highest amounts of total extract are obtained with highest alkaline conditions with pH 13.

The strong alkaline hydrolysis is performed e.g. between pH 11-14, more preferably between pH 11.5-14, more between pH 11.5-14, more between pH 12-14, more preferably more or about 13 with +/− marginal of 0.7, more preferably 0.5 and most preferably 0.3 pH units (e.g. pH between 9.7 and 10.3).

Preferably the reaction temperatures and times are as defined for the strong alkaline hydrolysis. In separately preferred embodiment the invention is directed to the preferred reaction where alkaline hydrolysis is first followed by acid hydrolysis (highest mannan total yield over 5% in examples 12 and 13) and in the other embodiment preferably acid hydrolysis is performed first and then alkaline hydrolysis. The strong alkaline hydrolysis reactions are preferred because of the highest yield of the relatively pure mannans.

Preferred Concentration of Acid in the Reaction

The present invention is directed to the use of minimum amount of the acid and base. The preferred final concentrations of the acid in the process depends on the amount of dry material in the reaction mixture. In a preferred embodiment the amount of yeast raw material as dry material is about 5-70%, more preferably 5-50%, more preferably 5-30% even more preferably 10-25%, even more preferably 15-25% or about 20%. It is realized that preferably concentrated spent yeast from fermentation process such as spent brewery yeast is used with concentration comprising preferred amount of yeast dry weight such as about 20% of dry weight. In another embodiment in medium concentrated as about 30% of dry weight, or in another embodiment in highly concentrated as about 40% of dry weight. The preferred medium range concentrations are from 20 to 40% of dry weight, more preferably from 22 to 38%, more preferably from 25 to 35%, even more preferably from 27 to 33% of dry weight. The preferred high range concentrations are from 30 to 60% dry weight, even more preferably from 30 to 50% of dry weight, even more preferably from 32 to 48%, even more preferably from 35 to 45%. In a preferred embodiment the present process includes a preferred acid and alkaline hydrolysis and a preferred concentration of yeast dry material is used, more preferably medium or high range concentrations or with any combinations thereof. The high concentrations are preferred to improve process effectiveness and energy efficiency. These or similar yeast raw material concentrations are preferred for alkaline hydrolysis.

The present invention is directed to optimized low acid amounts from about 0.1 to 0.75 M, more preferably 0.1-0.5 M, and higher acid amounts from about to be used with concentrated raw material or at lower pH ranges (e.g. pH 0.5-1.5), with higher concentration from about 0.5 M to 1.5 M, more preferably from 0.75 M to 1.25 M. In a preferred embodiment the low acid amounts and fosforic acid is used. It is realized that with the higher administered concentrations per volume in the reaction (final concentration) from about 0.3 M to about 2.0 M, more preferably from about 0.3 M to about 1.5 M, preferably from about 0.5 to about 1.5 M, or from 0.75 M to 1.25 M higher amounts are preferred to obtain higher solubilization of the preferred glycans.

Preferred final concentrations administered for preferred strong inorganic acids; hydrochloric acid, sulphuric acid or fosforic acid ($H_3PO_4$); are between 0.10 M to about 2.0 M from about 0.3 M to about 2.0 M, more preferably from about 0.30 M to about 1.5 M, preferably from about 0.5 to about 1.5 M, or from 0.75 M to 1.25 M and higher solubilization of the glycans is obtained, when the reaction is performed at temperature about 80 degrees of Celsius (preferably between 70-100 degrees of Celsius, even more preferably between 70 and 95 degrees of Celsius even more preferably between 75 and 85 degrees of Celsius. The preferred reaction time is about 4 hours, preferably from 2 to 8 hours, more preferably 3 to 5 hours, most preferably from 3.5 to 4.5 hours. In a preferred embodiment the final concentration range is used to adjust the pH to preferred value preferably between pH 1.5-4.0, more preferably between 2.0 and 3.5, even more preferably between 2.0 and 3.0.

Combined Acid and Alkaline Hydrolysis

The invention is directed to subjecting yeast cell material to a hydrolysis with an alkali at a pH about 9 to 14 and a temperature of about 10° to 100° C. for about 10 min to 8 hours and an acid at a pH about 1.5 to 4 and a temperature of about 30° to 100° C. for about 1 to 48 hours, neutralising the material, optionally contacting the material with an aqueous solution. In a preferred embodiment hydrolysis with an alkali is performed at a pH about 9 to 13 and a temperature of about 10° to 90° C. for about 10 min to 8 hours, and the acid hydrolysis is performed at a pH about 2 to 3 and a temperature of about 30° to 90° C. for about 3 to 48.

The invention is further directed to hydrolysis method, with the hydrolysis with an alkali at a pH about 9 to 13 and a temperature of about 10° to 90° C. for about 10 min to 8 hours, and the acid hydrolysis is performed at a pH about 2 to 3 and a temperature of about 30° to 90° C. for about 3 to 48 hours. The invention is further directed to hydrolysis method, wherein the hydrolysis with an alkali at a pH about 9 to 13 and a temperature of about 50° C. to 100° C. for about 0.5 h to 8 hours, and the acid hydrolysis is performed at a pH about 2 to 3 and a temperature of about 60° C. to 90° C. for about 1 to 4 hours.

The invention is further directed to hydrolysis method, wherein alkaline hydrolysis is performed by washing with alkaline solution pH 9-13 from 0.1 to 3 h more preferably between 10-45 degrees. The invention is further directed to hydrolysis method, wherein alkaline hydrolysis is performed between in pH 9-12.5, with reaction time from 1 h to 12 h, in temperature ranges are between 60-100 degrees of Celsius. The invention is further directed to hydrolysis method, wherein alkaline hydrolysis is performed between in pH 11.5-14, with reaction time from 1 h to 12 h, in temperature ranges are between 60-100 degrees of Celsius.

The invention is further directed to a soluble yeast mannan composition, wherein the saccharide fraction comprises beta1-6 glucan 0.001-10%, more preferably 0.005-5% and most preferably 0.01-3%, and most preferably 0.01-1.5% of the dry weight. The composition comprises mannan 5-25% or 10-20% w/w of the dry weight and the amount of β6-glucan or β-glucans is less than 5% w/w of the dry weight. The composition the composition comprises at least about 80 mol % of materials larger than 5000 Da and at highest 20 mol % of materials molecular weight between 1000 and 5000 Da, as shown by the Superdex gel filtration experiment, more preferably there is at least 85% material, more preferably at least 90% of the over 5000 Da material. The invention is further directed to the composition, wherein the amount of Manα3Manα2-comprising saccharides is at least 5% of all mannose epitopes, and more preferably at least 8% of all mannose epitopes, and more preferably at least 10% of all mannose epitopes, more preferably at least 15% of all mannose epitopes, more preferably at least 17% of all mannose epitopes, more preferably at least about 20% of all mannose epitopes, more preferably at least about 23% of all mannose epitopes (or structures), more preferably at least about 25% of all mannose epitopes (or structures more preferably at least about 28% of all mannose epitopes (or structures), as shown in the examples and Table 4. The invention is directed to the composition, wherein the composition has mannan starch/ratio at least about 0.95 and mannan/polypeptide ratio at least about 0.5 based on proton H1 signal integrals (as defined in example 14) and to other preferred rations for these.

The invention is especially directed to the preferred composition wherein the compositions are produced by using the methods according to the invention.

The invention is further directed to pretreatment of the materials including one or several selected from the group: 1) Autolysis, preferably by incubating the yeast raw material at pH between about 3-7 more preferably between 3.5 and 6.5, even more preferably between 4 and 6.5 for at least about 0.5-48 h, more preferably 1-24 h, even more preferably 2-16 h, at temperatures from 20 to 85 degrees of Celsius, more preferably 30 to 80 degrees of Celsius, in preferred embodiments between 30 and 60 degrees of Celsius or between 60 and 85 degrees of Celsius. Intact yeast (pH about 6) material was heat treated in examples 12 and 13 and showed some good results in Example 14. The invention is further directed using the alkaline washing as a pretreatment before the stronger alkaline and acid hydrolysis with good effects as implied by examples 12 and 13.

JP2006169514 is relatively close background with regard to alkaline hydrolysis, however the process uses very short acid reaction to precipitate protein, thus loosing material and the process leading of fraction containing substantially higher glucan amounts (no protein/peptide linked mannans). US2005020490 aims to production of pure mannan or glucan fractions without b6-glucan and the present acid hydrolysis to full yeast materials preferably without fractionation.

The invention will now be described in detail by way of reference only to the following non-limiting examples.

EXAMPLE 1

Processing of Brewer's Yeast According to the Process Shown in FIG. 1

Method

Yeast cell material (slurry consisting about 20% of dry matter) was treated with NaOH at pH 12 or 12.5 or 13 for 2 hours at +80° C., and thereafter cooled to room temperature. Then the material was treated with phosphoric acid ($H_3PO_4$) at pH 2.5 for 4 hours at +80° C., and then neutralized with NaOH at room temperature.

The material was diluted to 1% of dry matter with water and incubated under gentle mixing at room temperature for 2 hours. The mixture was centrifuged (3000 or 4000 rpm; 1811 or 3220 rcf, 5-20 min at RT), and the insoluble fraction was discarded. The supernatant was subjected to ultrafiltration in stirred ultrafiltration cell (Millipore) with ultrafiltration membranes (regenerated cellulose, Millipore) NMWL 1000 or 3000.

The soluble material of above MW 1000 or 3000 (depending on membrane in use) was lyophilized.

Commercial acid hydrolyzed yeast material was treated with 50 mM NaOH in 80% ethanol. Washings were discarded and 1% solution from the 80% ethanol insoluble fraction was prepared in water and incubated as described above.

Glucanex Treatment

Yeast cell material was hydrolysed with alkali and treated with Glucanex (lysing enzymes from *Trichoderma harzianum*, 1.18 U/g, Sigma) 1-4 mg/ml at +37° C. for 6-23 hours. The treatment was terminated by incubation at +80° C. for 0.5 h. Then material treated with acid and material was processed further as described in Example 1.

Method to Precipitate Phosphates

Phosphates generated in acid hydrolyzed yeast cell material after neutralization were precipitated with quantitative molar amount of $CaCl_2$ in slightly alkali solution pH 8.

General Method to Precipitate Soluble Products for Fractionation

Soluble components of yeast material after acid hydrolysis are precipitated with high concentrations (typically at least 80%) of low toxicity solvents such as alcohols, preferably EtOH or acetone, typically at temperatures about from 1-25 degree of Celsius, more preferably between 1-8 degrees of Celsius, from concentrated water solution of the soluble products such 1%, and preferably performing the precipitation from a preparation containing salts or from a preparation of yeast material after acid hydrolysis and $CaCl_2$ precipitation. The precipitation is optimized for isolation of the soluble yeast materials of invention as precipitate and for fractionation of lower molecular weight materials from the product.

The precipitate may contain salts which can be removed e.g by filtration or precipitated e.g. phosphates by $Ca2+$ ions after resolution of the precipitated soluble fraction.

Soluble fraction of acid hydrolyzed yeast cell material or $CaCl_2$ precipitated soluble fraction of acid hydrolyzed yeast cell material was incubated with acetone, essentially under conditions above, the precipitate is the product in method according to the invention.

EXAMPLE 2

The amount of soluble carbohydrate components in the product produced according to Example 1 was compared to a commercial acid hydrolyzed yeast material. 5 mg (dry weight) of the Example 1 type product and the commercial yeast material were dissolved in 0.7 ml of 99.9% deuterium oxide. After 1 h dissolving time, any insoluble matter was removed by centrifugation. 600 µl of solution was taken, and 0.5 µmol of phenylalanine methyl ester in deuterium oxide was added into both solutions as an internal standard quantitation standard. One-dimensional $^1$H-NMR spectra were collected using a Varian 500 MHz spectrometer operated at 296K.

The NMR spectra are presented in FIG. 3. Both spectra show the expected soluble carbohydrate components: Starch, yeast mannans, and yeast β1,6-glucans. Starch is detected by the Glcα1-4 residue H-1 signal at 5.40 ppm. The yeast mannan units reveal clearly assignable H-1 signals at 5.0-5.3 ppm:

(–2)Manα1-2 H-1 at 5.30 ppm, terminal Manα1-3 H-1 at 5.14 ppm, (–6)(–2)Manα1-6 H-1 at 5.12 ppm and (–2) Manα1-6 H-1 at 5.10 ppm. The large signal at 5.05 ppm contains the H-1 signals of (–6)Manα1-2, terminal Manα1-2 as well as (–3)Manα1-2. Yeast β1,6-glucans are revealed by the Glcβ1,6 residue H-1 signal at 4.53 ppm.

The amount of the soluble carbohydrate components were estimated by comparing the aromatic hydrogen signals of phenylalanine methyl ester to the H-1 signals of mannans. The meta- and para-position hydrogens were used for the analysis. Starch was not measured. Based on this analysis, 5 mg (dry weight) of the Example 1 product (FIG. 3A) yielded 4.4 µmol (0.7 mg) of Manα residues, while the 5 mg (dry weight) of the commercial yeast material (FIG. 3B) yielded 0.54 µmol (0.09 mg) of Manα residues. Thus the soluble part of Example 1 material contains 14% weight/weight of mannose and the commercial material 1.8% w/w (dry weight based weight %).

Both the material prepared as presented in Example 1 and the commercial acid hydrolyzed yeast material contained β1,6-glucans as revealed by the Glcβ1,6 H-1 signal at 4.53 ppm. Both materials were found to carry about 0.1 µmol (0.016 mg) of Glcβ residues per 5 mg of the dry sample. The amount of soluble β6-glucan was about 0.32% (w/w) of the total composition dry mass.

Only traces of β1,3-glucans (less than ⅕ or 20% of the amount of β1,6-glucans) were observed in both materials. The amount of β3-glucose structure containing soluble materials was thus about 0.0604% in certain preparation and depending of the process it may be totally removed. It is realized that this material is soluble and may contain other structures and is very different from regular yeast β3-glucan materials.

EXAMPLE 3

The size-profile of the soluble carbohydrate components in the material prepared as presented in Example 1 was obtained by reductive amination with 2-aminobenzamide followed by gel-filtration chromatography. One mg of the product material was dissolved in 1 ml of 0.2 M sodium borate buffer containing 100 µmol of 2-aminobenzamide and 0.5 M sodium cyanoborohydride. The reaction mixture was allowed to stand at 37° C. for 22 h. 0.2 mg aliquot of the product material was chromatographed on Superdex Peptide 10/300 GL column eluted at 1 ml/min with 100 mM ammonium bicarbonate. The eluting labeled material was detected by UV at 336 nm. The column was standardized by running similarly labeled dextran standards in identical chromatographic conditions.

FIG. 4 shows the elution pattern of the product material carbohydrates. The elution positions of dextran 5000 and dextran 1000 standards are indicated in the figure. The soluble saccharide fraction derived from samples prepared according to Example 1 had about 74% (prepared with alkali and acid; cut-off 1000 Da) and 87% (prepared with acid and alkali; cut-off 3000 Da) of >5000 Da and 26% and 13% of 1000-5000 Da oligo- and polysaccharides, respectively, calculated as area from the Superdex Peptide chromatogram of AB derivatized soluble material (absorbance units at 336 nm multiplied by elution volume).

EXAMPLE 4

The immunomodulatory activities of the material prepared as presented in Example 1 can be measured in vitro by human white blood cell assays essentially as described by Savolainen J, Nieminen K, Laaksonen K, Laiho T, Jacobsen L, Lahesmaa R, Terho E O, Valovirta E. Allergen-induced in vitro expression of IL-18, SLAM and GATA-3 mRNA in PBMC during sublingual immunotherapy. Allergy 62:949-53 (2007) and Wan C P, Park C S, Lau B H. A rapid and simple microfluorometric phagocytosis assay. J. Immunol. Methods. 162:1 (1993) and Busetto S, Trevisan E, Patriarca P, Menegazzi R. A single-step, sensitive flow cytofluorometric assay for the simultaneous assessment of membrane-bound and ingested *Candida albicans* in phagocytosing neutrophils. Cytometry A. 58:201 (2004).

To measure the cytokine modulation profile of the soluble fraction of yeast cell material processed according to invention, mononuclear cells (PBMC) are isolated from human peripheral blood. The PBMC are applied on cell culture plates and incubated in the presence of various concentrations of the material prepared according to FIG. 1 or 2 or Example 1 (e.g. 0.1, 1, 10 and 100 µg/ml). Specifically, PBMC can be collected from humans suffering from allergic reactions, and the PBMC can be stimulated with the pertinent allergen. The cultures are incubated in typical conditions, e.g. +37° C. in humidified atmosphere with 5% $CO_2$. After a suitable incubation time (e.g. 24-72 h), the cells and supernatants are collected. Total RNA can be extracted from the cells to measure the individual cytokine mRNA levels, e.g. by PCR techniques. Alternatively, from the cell culture supernatants the cytokines are measured at protein level e.g. by luminometric techniques. The informative cytokines include e.g. interleukins 4, 5, 10, 12, 13, 18 as well as interferon-γ.

The material prepared as shown in Example 1 stimulates phagocytotic activity of macrophages. This is measured by using macrophages obtained from mice or humans, or by using macrophage-type cell lines. Macrophages are cultured and then dispensed into e.g. 96-well plates, and incubated to allow cells to adhere to the wells in the presence of soluble fraction. Fluorescein conjugated pathogens, e.g. *E. coli* particles or living *C. albicans* cells are added and incubated for suitable period of time to allow phagocytosis to occur. Extracellular fluorescence can be quenched by adding trypan blue, which causes the typical green fluorescence of fluorescein-labeled cells to turn red. Phagocytosed cells retain the green fluorescence. The phagocytosis activity of the macrophages is thus measured by intensity of green fluorescence associated with ingested fluorescent cells. The fluorescence can be measured directly in the wells at 485 nm excitation and 530 nm emission. Alternatively, phagocytosis activity is measured by flow cytometry, where again green fluorescence indicates ingested pathogen cells and red fluorescence extracellular pathogens.

EXAMPLE 5

To measure the immunomodulatory activity of the Example 1 type product in vivo, a mouse animal trial is set up essentially as described in Smith A G, Sheridan P A, Harp J B, Beck M A. Diet-induced obese mice have increased mortality and altered immune responses when infected with influenza virus. J Nutr. 137:1236 (2007). A group of mice are fed with standard feed supplemented with the Example 1 material for a suitable period of time, preferably several weeks. A control group of mice are fed with standard feed only. Typical parameters are measured, including feed intake and body weight. Specifically, cytokine and IgA levels are measured as well as the phagocytosis activity of macrophages isolated from blood. Histological experiments are optionally conducted to analyze intestinal tract immune cells.

In order to analyze the effect of the diet on pathogen resistance, a challenge trial is set up. Mice are challenged e.g. by a suitable strain of influenza virus. The survival of mice is followed. If a non-lethal strain is used in the challenge, the infection severity is followed by e.g. viral titers in the respiratory tract or immunohistology of viral antigens in lung and brain. A control group of mice obtaining standard feed is used.

EXAMPLE 6

Use of the a soluble immunostimulatory composition that contains saccharide fraction in the Production of Healthy Snack Foods The soluble immunostimulatory composition that contains saccharide fraction from Example 1 or saccharide fraction alone is added at 0.5% (w/w) and 1% (w/w) to cookies, snack bars and bakery items. The soluble immunostimulatory composition that contains saccharide fraction supplemented cookies, snack bars and bakery items have more immunostimulatory effects than cookies, snack bars and bakery items not containing soluble immunostimulatory composition that contains saccharide fraction. Upon ingestion of the supplemented cookies, snack bars and bakery items, the soluble immunostimulatory composition that contains saccharide fraction are expected to stimulate the innate immune system of the intestinal tract and benefit the immune status of the consumer.

EXAMPLE 7

Brewer's yeast cell wall cream is processed according to Example 1 and soluble fraction is separated and spray dried or freeze dried. The saccharide fraction may be further isolated by e.g. chromatographic methods Examples.

The composition or saccharide fraction is a G.R.A.S. by the FDA. The composition can be used to supplement in a wide variety of foods with a high quality natural source of beta-1,6) glucans and mannans. This biologically active material stimulates the immune system of a mouse and protects against viral, bacterial and other microbe infections.

EXAMPLE 8

Use of Extracts in Animal Feed

A soluble immunostimulatory composition that contains saccharide fraction is produced according to Example 1.

This composition is used to supplement the diets of nursery pigs for e.g. 28 days post weaning. The supplement is blended with pig's feed and added used in various doses e.g. 0.05%, 0.1%, 0.2%, 0.3%, % 0.5% or 2% of total feed.

Control diets contain antibiotics. Post-weaned pigs (17-22 days old) are randomly allotted to the control diet or treatment diet based on body weight. After test period pigs are weighted. In a challenge experiment diarrhea causing $E.\ coli$ such as K88 $e\ coli$ is used.

EXAMPLE 9

Functional Beverages and Food

The soluble immunostimulatory composition that contains saccharide fraction according to the present invention can be added to drinks or food (e.g yoghurt) to improve the health of humans prone to infection such as immune-compromised individuals, athletes in intensive training, and, persons with hectic lifestyles or suffering from gastrointestinal tract problems. A suitable formulation for use as a non alcoholic beverage is: 25% juice content of carrot, tomato and/or orange 1% (w/v) soluble immunostimulatory composition that contains saccharide fraction preparation or 1% saccharide fraction alone.

It will be apparent to the person skilled in the art that while the invention has been described in some detail for the purposes of clarity and understanding, various modifications and alterations to the a embodiments and methods described herein may be made without departing from the scope of the inventive concept disclosed in this specification.

EXAMPLE 10

Use of the Soluble Immunostimulatory Composition that Contains Saccharide Fraction of Example 2 in Treatment of Eczema A select group of children suffering from eczema that is not responsive to current accepted skin lotion treatments is treated with a lotion containing e.g. a 1% suspension of the soluble immunostimulatory composition that contains saccharide fraction of Example 2. The lotion is applied twice daily. The skin is evaluated weekly by a dermatologist for improvement of lesions and pain. The soluble immunostimulatory composition that contains saccharide fraction lotion is expected to decrease the lesions associated pain and quickens the healing of the lesions.

EXAMPLE 11

Effect of the novel compositions for pathogen binding is optimized by studies of overlaying solid phase immobilized compositions (e.g as neoglycolipids) according to the invention by diarrhea causing labelled $E.\ coli$ and observing binding to compositions produced in example 1 and/or by other preferred methods of invention, or animal diarrhea causing pathogens and by inhibiting the bacteria binding to the compositions or to natural receptor glycans especially Manα-comprising neoglycolipids or lipids as described in PCT FI2003/00528.

EXAMPLE 12

Yeast cell material (slurry consisting about 20% of dry matter) was titrated with NaOH to a) pH 7, b) pH 10 or c) pH 13, and then incubated for 2.25 hours at +80° C. Control reaction was performed by incubating intact yeast material (pH ca. 6) similarly. The solutions were then cooled to room temperature, and treated with phosphoric acid ($H_3PO_4$) at pH 2.5 for 4.25 hours at +80° C., and then neutralized with NaOH at room temperature.

The solutions were diluted to 1% of dry matter with water and incubated under gentle mixing at room temperature for 2 hours. The mixture was centrifuged (3000 or 4000 rpm; 1811 or 3220 rcf, 5-20 min at RT), and the insoluble fraction was discarded. The supernatant was subjected to ultrafiltration in stirred ultrafiltration cell (Millipore) with ultrafiltration membranes (regenerated cellulose, Millipore) NMWL 1000, and the retentate was lyophilized. The yields of these extractions are presented in Table 1. The results show that a clear increase in >1000 Da material yield is obtained when the yeast material is treated first in alkaline solution. Most dramatically, if the yeast material is subjected to hydrolysis at pH 13, 2.7-fold increase in >1000 Da material is obtained.

EXAMPLE 13

Yeast cell material (slurry consisting about 20% of dry matter) was treated with phosphoric acid ($H_3PO_4$) at pH 2.5 for 4.25 hours at +80° C. The solutions were then cooled to room temperature, and titrated with NaOH to a) pH 7, b) pH 10 or c) pH 13, and then incubated for 2.25 hours at +80° C. Reaction were then neutralized with NaOH at room temperature. Control reaction A included only the acid hydrolysis step. Another control was performed, where the acid hydrolyzed material was lyophilized, and washed by a solution of 0.1M NaOH (nominal pH 13) in 80% ethanol. Washings were discarded.

One percent (w/v) solutions per dry matter were prepared in water and incubated under gentle mixing at room temperature for 2 hours. The mixture was centrifuged (3000 or 4000 rpm; 1811 or 3220 rcf, 5-20 min at RT), and the insoluble fraction was discarded. The supernatant was subjected to ultrafiltration in stirred ultrafiltration cell (Millipore) with ultrafiltration membranes (regenerated cellulose, Millipore) NMWL 1000, and the retentate was lyophilized. The yields of these extractions are presented in Table 1. The results show a clear increase in >1000 Da material yield when an alkaline hydrolysis is included. Washing of lyophilized acid hydrolyzed yeast material with alkaline ethanol solution removes some >1000 Da material as the yield is lower than in acid hydrolyzed material. However, as shown in Example 14 below, these are not primarily mannans, as the relative mannan yield is higher in the alkaline ethanol washed material.

EXAMPLE 14

The amount of soluble carbohydrate components in the products produced according to Examples 12 and 13 were analyzed by NMR. Five mg (dry weight) of each product and 1.0 µmol of phenylalanine methyl ester were dissolved in 0.6 ml of 99.9% deuterium oxide. One-dimensional $^1$H-NMR spectra were collected using a Varian 500 MHz spectrometer operated at 296K. Mannan H-1 signals as listed in Example 2 were integrated, and their area compared to the integrated area of aromatic protons of phenylalanine ring. The results of this quantitative analysis are presented in Table 2.

This analysis shows that the highest relative amount (purity) of mannans, 23.5% (w/w) of extracted product, is obtained in a process where yeast material is hydrolyzed first at pH 10 and then at pH 2.5, according to Example 12. High amount of mannans, 19.3% (w/w), is also obtained when the hydrolysis steps are reversed, as described in Example 13. However, highest total yield of the preferred mannans and highest amounts of total extract are obtained with highest alkaline conditions with pH 13.

The ratio of mannans to starch was also estimated from the NMR spectra. This data is collected in Table 3. This ratio was calculated from the integrated areas of mannan H-1 signals and integrated areas of starch derived H-1 signals (Glcα1-4 H-1 5.40 ppm, Glcα1-6 H-1 4.97 ppm). Here, it is evident that the processes including an alkaline hydrolysis followed by an acidic hydrolysis produce the highest mannan/starch ratio. Furthermore conditions with medium strong alkaline hydrolysis are preferred and the washing and heating at neutral or at about pH 6 (intact material) show improvement. Preferred mannan/starch ratios based on proton NMR H1 signals are at least about 0.85, more preferably at least about 0.90, more preferably at least about 0.95, more preferably at least about 1.0, more preferably at least about 1.1, more preferably at least about 1.2, more preferably at least about 1.25, more preferably at least about 1.3, more preferably at least about 1.3, more preferably at least about 1.4, more preferably at least about 1.5, more preferably at least about 1.6, more preferably at least about 1.7, more preferably at least about 1.8. About indicates variations of about 0.1 unit, more preferably 0.05 units, more preferably about 0.03 units.

The ratio of mannans to polypeptide material was estimated by comparing the mannan signal areas to an aliphatic proton signal area at 0.8-1.0 ppm. This proton-NMR signal area shows mostly methyl proton signals of aliphatic amino acids, e.g. valine, leucine and isoleucine. The mannan/polypeptide ratio data is presented in Table 3. The values represent ratio of the integral of Mannose H1 signals to the integral of aliphatic proton signals at 0.8-1.0 ppm (methyl proton signals). Of the extraction methods used here, the processes including a pH10 hydrolysis step seem to yield the lowest amount of aliphatic material signals. The washing procedure also produces low protein material. These products are preferred as low protein materials with high carbohydrate content. Higher relative peptinuos (peptide/protein) material contents from stronger alkaline hydrolysis would indicate soluble glycopeptide also with useful polyvalent glycan presentation capacity, when considering the amount of mannose in the preparations. The signals at highest pH products would indicate also a possibly soluble protein component. It should be emphasized that this analysis is not intended to give a real mannan/protein mass ratio, but a relative efficacy index for the extraction methods to produce higher purity mannans.

Preferred mannan/(poly)peptide ratios based on proton NMR H1 signals are at least about 0.45, more preferably at least about 0.40, more preferably at least about 0.45, more preferably at least about 0.5, more preferably at least about 0.55, more preferably at least about 0.60, more preferably at least about 0.65, most preferably at least about 0.70. About indicates variations of about 0.1 unit, more preferably 0.05 units, more preferably about 0.03 units.

The NMR spectra also allow an estimation of the Man-linkage ratios. These are calculated from the integrated signal areas of 5.31 ppm (–2Manα1-2 H-1), 5.14 ppm (terminal Manα1-3 H-1), 5.11 ppm (–2,6Manα1-6 H-1 and -2Manα1-6 H-1) and 5.04 ppm (–6Manα1-2 H-1, terminal Manα1-2 H-1 and -3Manα1-2 H-1). These integrated areas are collected on Table 4. In addition, the proportion of 5.14 ppm signal (comprising terminal Manα1-3 H-1) to all Man H-1 signals has been calculated. The data shows that the process slightly decreases the relative amount of terminal Manα3Manα2 depending on the alkaline strength giving preference for medium strength alkaline hydrolysis. On the other hand the products formed at high alkaline strength are more spaced between Manα3 like with Manα3Manα2Manα2 and have useful biological activities.

EXAMPLE 15

Increased Solubility, Lack of Taste and Odor

The products from example 12 and 13 are soluted to 2, 3, 4, 5, 6, 7, 8, 9, and 10% solutions. High and increased solubility is observed with acid alkaline processed materials. The invention is especially directed to materials of the invention which are soluble or essentially soluble as 2, 3, 4, 5, or 6% water solutions at room temperature. The invention is especially directed to highly soluble products from medium strong and strong alkaline hydrolysis being soluble (or essentially at least 95%, more preferably 97% soluble) at least with 2%, even more preferably with 4%, even more preferably with 5%, most preferably with 6% concentrations.

To test taste and odor present preparations are soluted to pure water as solutions with concentrations 1%, 0.5%, 0.1%, and 0.01%. Healthy normal test persons test the taste and odor and usually do not observe any (or any substantial) taste or odor with products at concentrations of lower than 0.5% concentration, or lower than 0.1% concentrations. The 1% solution may have some taste or odor but this is avoided in best processes.

TABLE 1

The extraction yields of soluble yeast products as described in Example 12 and Example 13.

| Sample | yield (mg)/gram of yeast dry matter |
|---|---|
| pH 7 - pH 2.5 - 1% - MWCO1000 | 139.5 |
| pH 10 - pH 2.5 - 1% - MWCO1000 | 139.4 |
| pH 13 - pH 2.5 - 1% - MWCO1000 | 280.5 |
| intact - pH 2.5 - 1% - MWCO1000 | 104.9 |
| pH 2.5 - 1% - MWCO1000 | 160.7 |
| pH 2.5 - lyophilization - NaOH/EtOH wash - 1% - MWCO1000 | 137.5 |
| pH 2.5 - pH 7 - 1% - MWCO1000 | 160.7 |
| pH 2.5 - pH 10 - 1% - MWCO1000 | 191.6 |
| pH 2.5 - pH 13 - 1% - MWCO1000 | 314.8 |

TABLE 2

The yields of yeast mannans prepared as described in Examples 12 and 13. Quantitation was carried out by proton-NMR experiment as described in Example 14.

| Sample | Yield Man (mg/5 mg product) | Yield Man (%, w/w) |
|---|---|---|
| pH 7 - pH 2.5 - 1% - MWCO1000 | 0.52 | 10.4 |
| pH 10 - pH 2.5 - 1% - MWCO1000 | 1.17 | 23.5 |
| pH 13 - pH 2.5 - 1% - MWCO1000 | 0.90 | 18.1 |
| intact - pH 2.5 - 1% - MWCO1000 | 0.82 | 16.3 |
| pH 2.5 - 1% - MWCO1000 | 0.46 | 9.3 |
| pH 2.5 - lyophilization - NaOH/EtOH wash - 1% - MWCO1000 | 0.75 | 14.9 |
| pH 2.5 - pH 7 - 1% - MWCO1000 | 0.71 | 14.1 |
| pH 2.5 - pH 10 - 1% - MWCO1000 | 0.97 | 19.3 |
| pH 2.5 - pH 13 - 1% - MWCO1000 | 0.67 | 13.5 |

TABLE 3

The ratio of mannans in the yeast extracts as compared to starch and polypeptide-type material.

| Sample | Mannan/starch ratio | Mannan/polypeptide material ratio |
|---|---|---|
| pH 7 - pH 2.5 - 1% - MWCO1000 | 0.83 | 0.22 |
| pH 10 - pH 2.5 - 1% - MWCO1000 | 1.59 | 0.70 |
| pH 13 - pH 2.5 - 1% - MWCO1000 | 1.78 | 0.33 |
| intact - pH 2.5 - 1% - MWCO1000 | 0.96 | 0.35 |
| pH 2.5 - 1% - MWCO1000 | 0.82 | 0.32 |
| pH 2.5 - lyophilization - NaOH/EtOH wash - 1% - MWCO1000 | 0.90 | 0.48 |
| pH 2.5 - pH 7 - 1% - MWCO1000 | 0.95 | 0.42 |
| pH 2.5 - pH 10 - 1%- MWCO1000 | 1.26 | 0.66 |
| pH 2.5 - pH 13 - 1% - MWCO1000 | 0.65 | 0.33 |

The abundancies were measured from proton-NMR spectra as described in Example 14. The mannan/polypeptide material ratio is intended to describe the ratio within this extraction series, i.e. the efficacy of the shown extraction types to isolate mannans. This is not a quantitative mannan/protein ratio.

TABLE 4

The ratio of Man residues in the yeast extracts prepared as described in Examples 12 and 13.

| | -2Manα1-2 H-1 5.31 ppm | Manα1-3 H-1 5.14 ppm | -2,6Manα1-6 H-1 -2Manα1-6 H-1 5.11 ppm | -6Manα1-2 H-1 Manα1-2 H-1 -3Manα1-2 H-1 5.04 ppm | Manα1-3% |
|---|---|---|---|---|---|
| pH 7 - pH 2.5 - 1% - MWCO1000 | 100.00 | 179 | 97.0 | 191 | 31.6 |
| pH 10 - pH 2.5 - 1% - MWCO1000 | 100.00 | 170 | 106.0 | 191 | 30.0 |
| pH 13 - pH 2.5 - 1% - MWCO1000 | 100.00 | 125 | 88.0 | 125 | 28.5 |
| Intact - pH 2.5 - 1% - MWCO1000 | 100.00 | 175 | 87.0 | 187 | 31.9 |
| pH 2.5 - 1% - MWCO1000 | 100.00 | 153 | 86.0 | 180 | 29.5 |
| pH 2.5 - lyophilization - NaOH/EtOH wash - 1% - MWCO1000 | 100.00 | 146 | 92.0 | 170 | 28.7 |
| pH 2.5 - pH 7 - 1% - MWCO1000 | 100.00 | 172 | 90.0 | 184 | 31.5 |
| pH 2.5 - pH 10 - 1% - MWCO1000 | 100.00 | 162 | 92.0 | 174 | 30.7 |
| pH 2.5 - pH 13 - 1% - MWCO1000 | 100.00 | 129 | 87.0 | 155 | 27.4 |

The integrated area of signal 5.31 ppm (-2Manα1-2 H-1) was set to 100.

The invention claimed is:

1. A soluble immunostimulatory composition comprising an effective amount of soluble fraction produced by a method comprising the steps of:
   (i) providing yeast cell wall material;
   (ii) subjecting the yeast cell wall material to hydrolysis with alkali at a pH of 9 to 14, followed by hydrolysis with acid at pH 1.5 to 4, and then optionally neutralizing the hydrolyzed material; and
   (iii) separating a soluble fraction from the hydrolyzed material obtained in step (ii);
   wherein the soluble fraction obtained in step iii) comprises starch, water-soluble mannan in an amount from 5-25% w/w dry weight of the total soluble fraction, and water-soluble beta-1-6 glucan in an amount from 0.001-10% w/w dry weight of a total soluble fraction,
   wherein the water-soluble mannan comprises mannose epitopes and at least 5% of the mannose epitopes are Manα3Manα2-containing saccharides, and
wherein the soluble fraction has a mannan/starch ratio of at least about 0.95.

2. The composition of claim 1, wherein the amount of Manα3Manα2-containing saccharides is at least 5%.

3. The composition of claim 1, wherein
   step ii) comprises subjecting said yeast cell wall material to hydrolysis with alkali at a pH 9 to 14 and a temperature of 10° to 100° C. for 10 min to 18 hours and hydrolysis with acid at a pH 1.5 to 4 and a temperature of 30° to 100° C. for 1 to 48 hours, and then neutralising the hydrolyzed material.

4. The composition of claim 1, wherein the soluble fraction obtained in step iii) is subjected to further fractionation.

5. The composition of claim 4, wherein said fractionation is performed by chromatography, phase separation, precipitation, or ultrafiltration.

6. The composition of claim 5, wherein said fractionation is performed by ultrafiltration.

7. The composition of claim 6, wherein the ultrafiltration is performed with a membrane cut-off of at least 500 Da to obtain an ultrafiltrated soluble saccharide fraction.

8. The composition of claim 1, wherein the soluble fraction comprises water-soluble beta 1-6 glucan in an amount from 0.005-5% w/w dry weight of the total soluble fraction.

9. The composition of claim 1, wherein the soluble fraction comprises water-soluble beta1-6 glucan in an amount from 0.01-3% w/w dry weight of the total soluble fraction.

10. The composition according to claim 1, wherein the composition is selected from the group consisting of: food supplement, pharmaceutical, nutraceutical, and animal feed.

11. A method of treating a subject in need of immunostimulation, comprising administering to the subject an effective amount of the composition according to claim 1.

12. A method for producing a soluble immunostimulatory composition that contains a soluble saccharide fraction, comprising the steps of:
   (i) providing yeast cell wall material;
   (ii) subjecting the yeast cell wall material to hydrolysis with alkali at a pH of 9 to 14, followed by hydrolysis with acid at pH 1.5 to 4, and then optionally neutralizing the hydrolyzed material; and
   (iii) separating a soluble fraction from the hydrolyzed material obtained in step (ii);
   wherein the soluble fraction obtained in step iii) comprises starch, water-soluble mannan in an amount from 5-25% w/w dry weight of the total soluble fraction, and water-soluble beta-1-6 glucan in an amount from 0.001-10% w/w dry weight of a total soluble fraction,
   wherein the water-soluble mannan comprises mannose epitopes and at least 5% of the mannose epitopes are Manα3Manα2-containing saccharides, and
   wherein the soluble fraction has a mannan/starch ratio of at least about 0.95.

13. The method of claim 12, further comprising step iv) subjecting the soluble fraction of step iii) to fractionation.

14. The method of claim 12, wherein water solubility of the composition is at least 95%.

15. The method of claim 12, wherein material is not fractionated between acid and alkaline hydrolysis in step ii), or wherein material is fractionated between hydrolysis with acid and alkaline in step ii) and both soluble and non-soluble fractions are subjected to a second hydrolysis.

16. The method of claim 12, wherein step (ii) comprises subjecting the yeast cell wall material to hydrolysis with alkali at a pH of 9 to 14 at a temperature of 10° C. to 100° C. for 10 minutes to 18 hours, followed by hydrolysis with acid at pH 1.5 to 4 at a temperature of 30° C. to 100° C. for 1 to 48 hours, and then neutralizing the hydrolyzed material.

17. The method of claim 13, wherein said fractionation is performed by ultrafiltration with a membrane cut-off of at least 500 Da to obtain an ultrafiltrated soluble saccharide fraction.

18. A composition produced by the method of claim 12, wherein the saccharide fraction comprises 1,6-linked glucose monomers and mannans, and wherein the ratio of 1,6-linked glucose monomers and mannans is 1 to 40 and optionally wherein the saccharide fraction comprises β1-6 glucan 0.001-10% of the dry weight and mannan 1.0-50% of the dry weight.

* * * * *